United States Patent
Bamford et al.

(10) Patent No.: US 7,452,906 B2
(45) Date of Patent: Nov. 18, 2008

(54) PYRIDINE DERIVATIVES AS RAF KINASE INHIBITORS

(75) Inventors: Mark James Bamford, Harlow (GB); David Kenneth Dean, Harlow (GB); Antoinette Naylor, Harlow (GB); Andrew Kenneth Takle, Harlow (GB); David Matthew Wilson, Harlow (GB)

(73) Assignee: SmithKline Beecham P.L.C., Brentford, Middlesex (GB)

( * ) Notice: Subject to any disclaimer, the term of this patent is extended or adjusted under 35 U.S.C. 154(b) by 366 days.

(21) Appl. No.: 10/488,580

(22) PCT Filed: Sep. 5, 2002

(86) PCT No.: PCT/EP02/09946

§ 371 (c)(1),
(2), (4) Date: Mar. 4, 2004

(87) PCT Pub. No.: WO03/022840

PCT Pub. Date: Mar. 20, 2003

(65) Prior Publication Data

US 2004/0235843 A1   Nov. 25, 2004

(30) Foreign Application Priority Data

Sep. 5, 2001   (GB) .................. 0121490.7

(51) Int. Cl.
*A61K 31/445*   (2006.01)
*C07D 401/14*   (2006.01)
*C07D 405/14*   (2006.01)
*C07D 413/14*   (2006.01)

(52) U.S. Cl. .................. 514/318; 514/242; 514/252.05; 514/255.05; 514/256; 514/336; 514/342; 514/343; 544/238; 544/328; 544/405; 546/193; 546/268; 546/272.7

(58) Field of Classification Search .................. 514/242, 514/252.05, 255.05, 256, 336, 342.343, 318; 544/238, 328, 405; 546/268, 272.7, 193
See application file for complete search history.

(56) References Cited

FOREIGN PATENT DOCUMENTS

| GB | 2 306 108 | 4/1997 |
|---|---|---|
| WO | WO 95/03297 | 2/1995 |
| WO | WO 02/24680 | 3/2002 |

OTHER PUBLICATIONS

Dluzniewska et al. "Transient cerebral ishemiia . . . " SciSearch 13712750 (2005).*
Wermuth "The practice of medicinal chemistry" Acd. Press p. 203-213 (1996).*
Grever et al. "The national cancer institute . . . " Seminars in oncology v. 19, p. 622-638 (1992).*
Lange et al. "Bioisosteric replacement . . . " J. Med. Chem. v48, 1823-1838 (2005).*
IlaSircar et al. "Nonpeptide angiotensin II . . . " J. Med. Chem. v. 36, p. 2253-65 (1993).*
Keller et al. "The role of Raf kinase . . . " Biochem. Pharm. v.68, pp. 1049-1053 (2004).*
Merck Index p. 4149, 4811 (1979).*
Kelley et al. "Synthesis and . . . " J. Med. chem. v.38, p. 3884-3888(1995).*

* cited by examiner

*Primary Examiner*—Celia Chang
(74) *Attorney, Agent, or Firm*—Grace C. Hsu; Mary E. McCarthy; Charles M. Kinzig

(57) ABSTRACT

Compounds and their use as pharmaceuticals particularly as Raf kinase inhibitors for the treatment of neurotraumatic diseases, cancer, chronic neurodegeneration, pain, migraine and cardiac hypertrophy.

6 Claims, No Drawings

PYRIDINE DERIVATIVES AS RAF KINASE INHIBITORS

This application is a §371 national stage filing of PCT/EP02/09946 filed 5 Sep. 2002.

This invention relates to novel compounds and their use as pharmaceuticals, particularly as Raf kinase inhibitors for the treatment of neurotraumatic diseases, cancer, chronic neurodegeneration, pain, migraine and cardiac hypertrophy.

Raf protein kinases are key components of signal transduction pathways by which specific extracellular stimuli elicit precise cellular responses in mammalian cells. Activated cell surface receptors activate ras/rap proteins at the inner aspect of the plasma-membrane which in turn recruit and activate Raf proteins. Activated Raf proteins phosphorylate and activate the intracellular protein kinases MEK1 and MEK2. In turn, activated MEKs catalyse phosphorylation and activation of p42/p44 mitogen-activated protein kinase (MAPK). A variety of cytoplasmic and nuclear substrates of activated MAPK are known which directly or indirectly contribute to the cellular response to environmental change. Three distinct genes have been identified in mammals that encode Raf proteins; A-Raf, B-Raf and C-Raf (also known as Raf-1) and isoformic variants that result from differential splicing of mRNA are known.

Inhibitors of Raf kinases have been suggested for use in disruption of tumor cell growth and hence in the treatment of cancers, e.g. histiocytic lymphoma, lung adenocarcinoma, small cell lung cancer and pancreatic and breast carcinoma; also in the treatment and/or prophylaxis of disorders associated with neuronal degeneration resulting from ischemic events, including cerebral ischemia after cardiac arrest, stroke and multi-infarct dementia and also after cerebral ischemic events such as those resulting from head injury, surgery and/or during childbirth; also in chronic neurodegeneration such as Alzheimer's disease and Parkinson's disease; also in the treatment of pain, migraine and cardiac hypertrophy.

We have now found a group of novel compounds that are inhibitors of Raf kinases, in particular inhibitors of B-Raf kinase.

According to the invention there is provided compounds of formula (I):

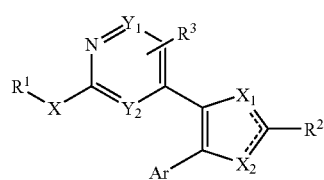

(I)

wherein $X$ is O, $CH_2$, CO, S or NH, or the moiety $X-R^1$ is hydrogen;

$Y_1$ and $Y_2$ independently represent CH or N;

$R^1$ is hydrogen, $C_{1-6}$alkyl, $C_{3-7}$cycloalkyl, aryl, aryl $C_{1-6}$alkyl-, heterocyclyl, heterocyclyl$C_{1-6}$alkyl-, heteroaryl, or heteroaryl$C_{1-6}$alkyl-, any of which, except hydrogen, may be optionally substituted;

$R^2$ is $C_{1-6}$alkyl, $C_{3-7}$cycloalkyl, heterocyclyl, heterocyclyl$C_{1-6}$alkyl-, hetero$C_{1-6}$alkyl-, or $C_{1-6}$alkylhetero $C_{1-6}$alkyl-any of which may be optionally substituted;

Ar is a group of the formula a) or b):

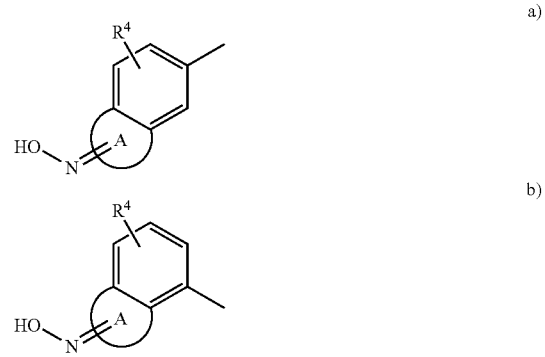

wherein A represents a fused 5- to 7-membered ring optionally containing up to two heteroatoms selected from O, S and $NR^5$, wherein $R^5$ is hydrogen or $C_{1-6}$alkyl, which ring is optionally substituted by up to 2 substituents selected from halogen, $C_{1-6}$alkyl, hydroxy, $C_{1-6}$alkoxy or keto;

$R^3$ and $R^4$ are independently selected from hydrogen, halogen, $C_{1-6}$alkyl, aryl, aryl$C_{1-6}$alkyl, $C_{1-6}$alkoxy, $C_{1-6}$alkoxy$C_{1-6}$alkyl, halo$C_{1-6}$alkyl, aryl$C_{1-6}$alkoxy, hydroxy, nitro, cyano, azido, amino, mono- and di-N-$C_{1-6}$alkylamino, acylamino, arylcarbonylamino, acyloxy, carboxy, carboxy salts, carboxy esters, carbamoyl, mono- and di-N-$C_{1-6}$alkylcarbamoyl, $C_{1-6}$alkoxycarbonyl, aryloxycarbonyl, ureido, guanidino, $C_{1-6}$alkylguanidino, amidino, $C_{1-6}$alkylamidino, sulphonylamino, aminosulphonyl, $C_{1-6}$alkylthio, $C_{1-6}$alkylsulphinyl or $C_{1-6}$alkylsulphonyl; and one of $X_1$ and $X_2$ is selected from O, S or $NR^{11}$ and the other is CH, wherein $R^{11}$ is hydrogen, $C_{1-6}$alkyl, aryl or aryl$C_{1-6}$alkyl;

or pharmaceutically acceptable salts thereof.

As used herein, the double bond indicated by the dotted lines of formula (I), represents the possible regioisomeric ring forms of the compounds falling within the scope of this invention, the double bond being between the non-hetero-atoms.

The hydroxyimino moiety can be positioned on any of carbon atoms of the non-aromatic ring in groups a) and b).

The hydroxyimino moiety can exist as either the E or Z isomer or as a mixture of both. Alkyl and alkenyl groups referred to herein, individually or as part of larger groups e.g. alkoxy, may be straight or branched groups containing up to six carbon atoms and are optionally substituted by one or more groups selected from the group consisting of aryl, heteroaryl, heterocyclyl, $C_{1-6}$alkoxy, $C_{1-6}$alkylthio, aryl $C_{1-6}$alkoxy, aryl$C_{1-6}$alkylthio, amino, mono- or di-$C_{1-6}$alkylamino, cycloalkyl, cycloalkenyl, carboxy and esters thereof, amide, sulphonamido, ureido, guanidino, $C_{1-6}$alkylguanidino, amidino, $C_{1-6}$alkylamidino, $C_{1-6}$acyloxy, azido, hydroxy, hydroxyimino and halogen.

Cycloalkyl and cycloalkenyl groups referred to herein include groups having from three to seven ring carbon atoms and are optionally substituted as described hereinabove for alkyl and alkenyl groups.

When used herein, the term "aryl" includes, unless otherwise defined, single and fused rings suitably containing from 4 to 7, preferably 5 or 6, ring atoms in each ring, which rings, may each be unsubstituted or substituted by, for example, up to three substituents.

Suitable aryl groups include phenyl and naphthyl, such as 1-naphthyl or 2-naphthyl.

Optional substituents for alkyl, alkenyl, cycloalkyl and cycloalkenyl groups include aryl, heteroaryl, heterocyclyl, $C_{1-6}$alkoxy, $C_{1-6}$alkylthio, aryl$C_{1-6}$alkoxy, aryl$C_{1-6}$alkylthio, amino, mono-or di-$C_{1-6}$alkylamino, aminosulphonyl, cycloalkyl, cycloalkenyl, carboxy and esters thereof, amide, ureido, quanidino, $C_{1-6}$alkylquanidino, amidino, $C_{1-6}$alkylamidino, $C_{1-6}$acyloxy, hydroxy, and halogen or any combination thereof. Preferably the substituents are mono-or di-$C_{1-6}$allylamino, heterocyclo$C_{1-6}$alkylamino or $C_{2-6}$acylamino.

Alternatively the optional substituent contains a water-solubilising group; suitable solubilising moieties will be apparent to those skilled in the art and include hydroxy and amine groups. Even more preferably the optional substituent includes amino, mono- or di-$C_{1-6}$alkylamino, amine containing heterocyclyl, or hydroxy or any combination thereof.

When used herein the term "heterocyclyl" includes, unless otherwise defined, non-aromatic, single and fused, which rings may be saturated or unsaturated rings, suitably containing up to four heteroatoms in each ring, each of which is selected from O, N and S, which rings, may be unsubstituted or substituted by, for example, up to three substituents. Each heterocyclic ring suitably has from 4 to 7, preferably 5 or 6, ring atoms. A fused heterocyclic ring system may include carbocyclic rings and need include only one heterocyclic ring. Examples of heterocyclyl groups include pyrrolidine, piperidine, piperazine, morpholine, thiomorpholine, imidazolidine and pyrazolidine wherein any one of the groups piperidine, piperazine, morpholine and thiomorpholine can have at least one double bond.

When used herein, the term "heteroaryl" includes, unless otherwise defined, mono- and bicyclic heteroaromatic ring systems comprising up to four, preferably 1 or 2, heteroatoms each selected from O, N and S. Each ring may have from 4 to 7, preferably 5 or 6, ring atoms. A bicyclic heteroaromatic ring system may include a carbocyclic ring. Examples of heteroaryl groups include pyrrole, quinoline, isoquinoline, pyridine, pyrimidine, oxazole, thiazole, thiadiazole, triazole, imidazole and benzimidazole.

When used herein heteroC$_{1-6}$alkyl- means a $C_{1-6}$ carbon chain wherein the end carbon atom in the chain is substituted by a heteroatom selected from N, O, or S for example $C_{1-6}$alkylamino, $C_{1-6}$alkyloxy or $C_{1-6}$alkylthio.

$C_{1-6}$alkylheteroC$_{1-6}$alkyl means a $C_{3-13}$alkyl chain wherein one of the carbon atoms has been replaced with a heteroatom selected from N, O, or S, for example $C_{1-6}$alkylamino$C_{1-6}$alkyl or $C_{1-6}$ alkylaminodi$C_{1-6}$alkyl, $C_{1-6}$alkyloxy$C_{1-6}$alkyl-, $C_{1-6}$alkylthio$C_{1-6}$alkyl-, or $C_{1-6}$ alkylthiodi$C_{1-6}$alkyl.

Aryl, heterocyclyl and heteroaryl groups may be optionally substituted by preferably up to three substituents. Suitable substituents include halogen, hydroxy, $C_{1-6}$alkyl, aryl, aryl $C_{1-6}$alkyl, $C_{1-6}$alkoxy, $C_{1-6}$alkoxy$C_{1-6}$alkyl, halo $C_{1-6}$alkyl, aryl$C_{1-6}$alkoxy, hydroxy, nitro, cyano, azido, amino, mono- and di-N-$C_{1-6}$alkylamino, acylamino, arylcarbonylamino, acyloxy, carboxy, carboxy salts, carboxy esters, carbamoyl, mono- and di-N-$C_{1-6}$alkylcarbamoyl, $C_{1-6}$alkoxycarbonyl, aryloxycarbonyl, ureido, guanidino, $C_{1-6}$alkylguanidino, amidino, $C_{1-6}$alkylamidino, sulphonylamino, aminosulphonyl, $C_{1-6}$alkylthio, $C_{1-6}$alkylsulphinyl, $C_{1-6}$alkylsulphonyl, heterocyclyl, heteroaryl, heterocyclyl $C_{1-6}$alkyl, hydroxyimino-$C_{1-6}$alkyl and heteroaryl $C_{1-6}$alkyl, and combinations thereof.

Preferably the optional substituent contains a water-solubilising group; suitable solubilising moieties will be apparent to those skilled in the art and include hydroxy and amine groups. Even more preferably the optional substituent includes amino, mono- or di-$C_{1-6}$alkylamino, amine containing heterocyclyl, or hydroxy or any combination thereof.

When used herein the term halo represents fluoro, chloro, bromo or iodo.

X is preferably NH or X—$R^1$ is preferably hydrogen and when X is NH, $R^1$ is preferably hydrogen or $C_{1-6}$alkyl.

When $Y_1$ and $Y_2$ are CH, X—$R^1$ is preferably hydrogen.
When $Y_2$ is N, $R^1$ is preferably H or $C_{1-6}$alkyl.
Most preferably X—$R^1$ is hydrogen
Preferably $X_1$ or $X_2$ is S or O, more preferably O.
Preferably $R^{11}$ is hydrogen.

A is preferably a fused 5 membered ring optionally containing up to two heteroatoms selected from O, S and $NR^5$, wherein $R^5$ is hydrogen or $C_{1-6}$alkyl, which ring is optionally substituted by up to 2 substituents selected from halogen, $C_{1-6}$alkyl, hydroxy, $C_{1-6}$alkoxy or keto.

Even more preferably A is a fused 5 membered ring.
Preferably $R^2$ is an optionally substituted heterocyclyl, heterocyclyl($C_{1-6}$)alkyl- or $C_{1-6}$alkylheteroC$_{1-6}$alkyl.

Most preferably the compounds of the invention are of formula (II);

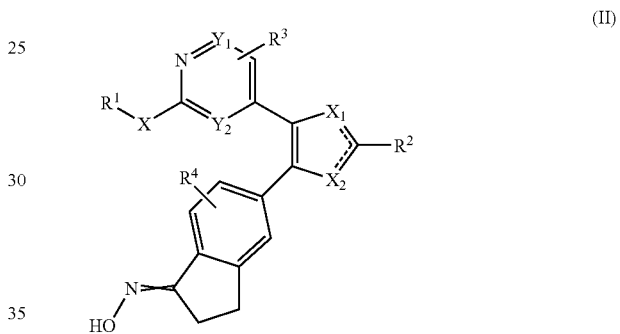

(II)

wherein $R^1$, X, $Y_1$, $Y_2$, $R^3$, $X_1$, $X_2$, $R^2$ and $R^4$ are as described for compounds of formula (I).

The compounds of formula (I) preferably have a molecular weight of less than 800.

Preferred substituents for the group Ar include halo, hydroxy, hydroxyC$_{1-6}$alkyl, hydroxyimino-$C_{1-6}$alkyl and $C_{1-6}$alkoxy.

It will be understood that the invention includes pharmaceutically acceptable derivatives of compounds of formula (I) and that these are included within the scope of the invention.

Particular compounds according to the invention include those mentioned in the examples and their pharmaceutically acceptable salts. As used herein "pharmaceutically acceptable derivatives" includes any pharmaceutically acceptable salt, ester or salt of such ester of a compound of formula (I) which, upon administration to the recipient, is capable of providing (directly or indirectly) a compound of formula (I) or an active metabolite or residue thereof.

It will be appreciated that for use in medicine the salts of the compounds of formula (I) should be pharmaceutically acceptable. Suitable pharmaceutically acceptable salts will be apparent to those skilled in the art and include those described in *J. Pharm. Sci.*, 1977, 66, 1-19, such as acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluenesulfonic, methanesulfonic or naphthalenesulfonic acid. Other salts e.g. oxalates, may be used, for example in the isolation of compounds of formula (I) and are included within the scope of this invention.

The compounds of this invention may be in crystalline or non-crystalline form, and, if crystalline, may optionally be hydrated or solvated. This invention includes within its scope stoichiometric hydrates as well as compounds containing variable amounts of water.

The invention extends to all isomeric forms including stereoisomers and geometric isomers of the compounds of formula (I) including enantiomers and mixtures thereof e.g. racemates. The different isomeric forms may be separated or resolved one from the other by conventional methods, or any given isomer may be obtained by conventional synthetic methods or by stereospecific or asymmetric syntheses.

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

Compounds of formula (I) are furan, pyrrole and thiophene derivatives which may be readily prepared, using procedures well-known to those skilled in the art, from starting materials which are either commercially available or can be prepared from such by analogy with well-known processes. For instance see, W. Friedrichsen (p 351, furans), R. J. Sundberg (p 119, pyrroles) and J. Nakayama (p 607, thiophenes) in *Comprehensive Heterocyclic Chemistry II*, volume 2, series eds. A. R. Katritzky, C. W. Rees and E. F. V. Scriven. Typically, compounds of this invention may be prepared by a Paal-Knorr synthesis from a 1,4-dicarbonyl precursor, as outlined in Scheme 1 (where the groups $R^1X$, $R^3$, and $R^4$ are hydrogen, and $Y_1$ and $Y_2$ are CH). For example, base (e.g. diethylamine) mediated condensation of a methyl-ketone derivative with pyridine-4-carboxaldehyde results in the formation of a chalcone derivative (1, see S. E. deLaszlo et al. *Bioorg. Med. Chem. Lett.*, 1999, 9, 641). Subsequent reaction of the chalcone (1) with a suitably protected (e.g. a methoxyimine, PG=MeON) derivative of indan-1-one-5-carboxaldehyde and catalytic sodium cyanide under Stetter conditions (H. Stetter and K. Kuhlmann, *Org. React.*, 1991, 40, 407) generates the aforementioned 1,4-dicarbonyl precursor (2). Cyclisation under the appropriate conditions then results in the formation of the desired furan (e.g. phosphorus pentoxide-methanesulphonic acid, concentrated sulphuric acid or HCl/acetone/dioxan), pyrrole (e.g. ammonium acetate, acetic acid) or thiophene (e.g. Lawessons reagent) ring systems (3). Thereafter, the group $R^{2'}$ may be converted into another group $R^2$, using conventional functional group interconversion procedures, and the group PG converted into an hydroxyimino group as in (4). It will also be appreciated to one skilled in the art, that the aldehyde components could be utilised in reverse order generating the chalcone derivative (5) and subsequently the regioisomeric heterocycles (6).

Scheme 1

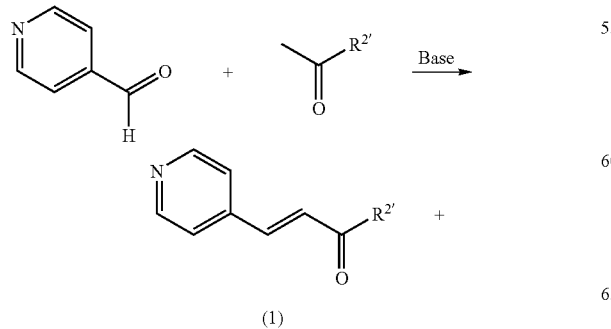

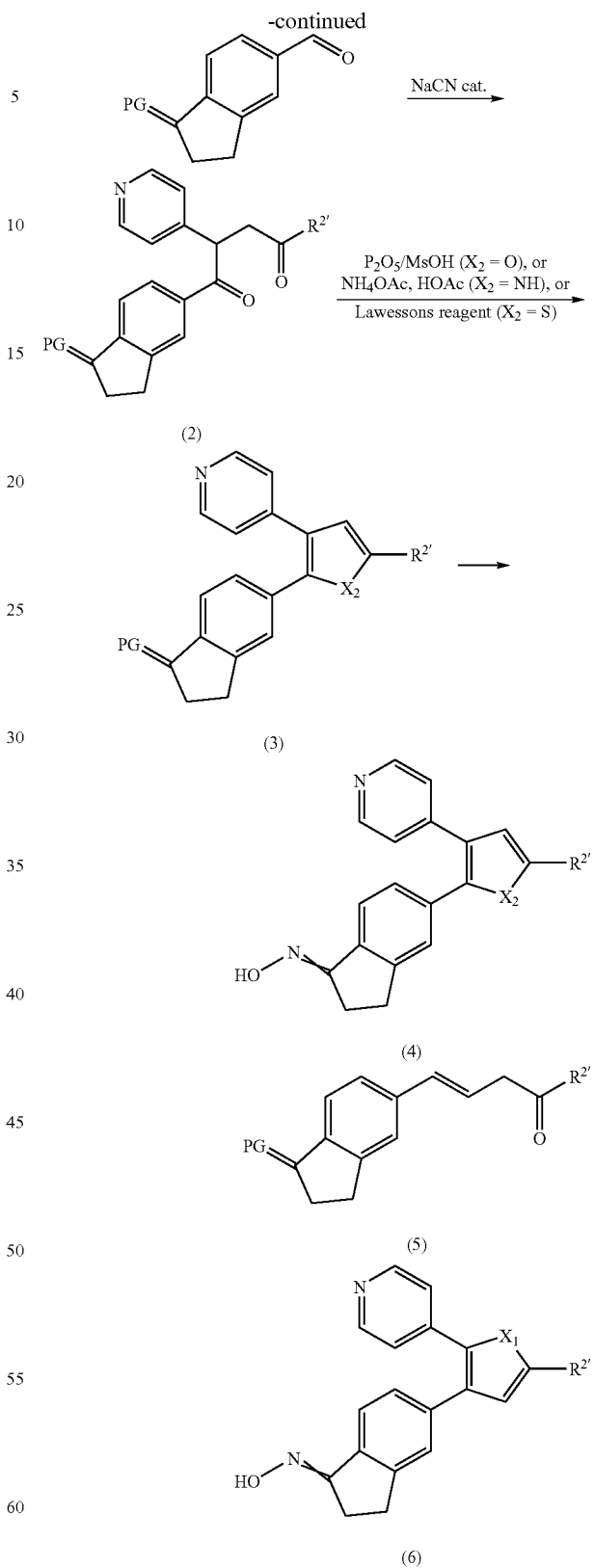

Compounds of this invention may also be prepared by sequential transition metal catalysed cross-coupling reactions on a 2,3-dihalo heterocycle, as shown in Scheme 2; this is particularly applicable for furan or thiophene derivatives, i.e. when one of $X_1$ or $X_2$ are O or S. For example, Suzuki coupling of pyridine-4-boronic acid with a 2,3-dibromofuran derivative (7) preferentially results in the formation of the 2-(4-pyridyl)-3-bromo-furan (8). Subsequent Suzuki reaction with an indanone boronic acid derivative (9, wherein PG is O, N-OMe or another ketone protecting group) generates the derivative (10). Thereafter, the group $R^{2'}$ may be converted into a group $R^2$ using appropriate conventional functional group interconversion procedures. For example, treatment of (10, where $R^{2'}$ is hydrogen) with n-butyl lithium generates the corresponding metallated derivative (10, where $R^{2'}$ is Li) which can be reacted with a variety of electrophiles (such as N)N-dimethylformamide) generating derivatives (10, where $R^{2'}$ is CHO) which allow further modification by, for example, reductive-amination procedures. Subsequently the group PG can also be converted into an hydroxyimino group as in (11). It will also be appreciated, to one skilled in the art, that the above cross-coupling reactions may be carried out in reverse order giving access to the regioisomeric heterocycles (12).

Scheme 2

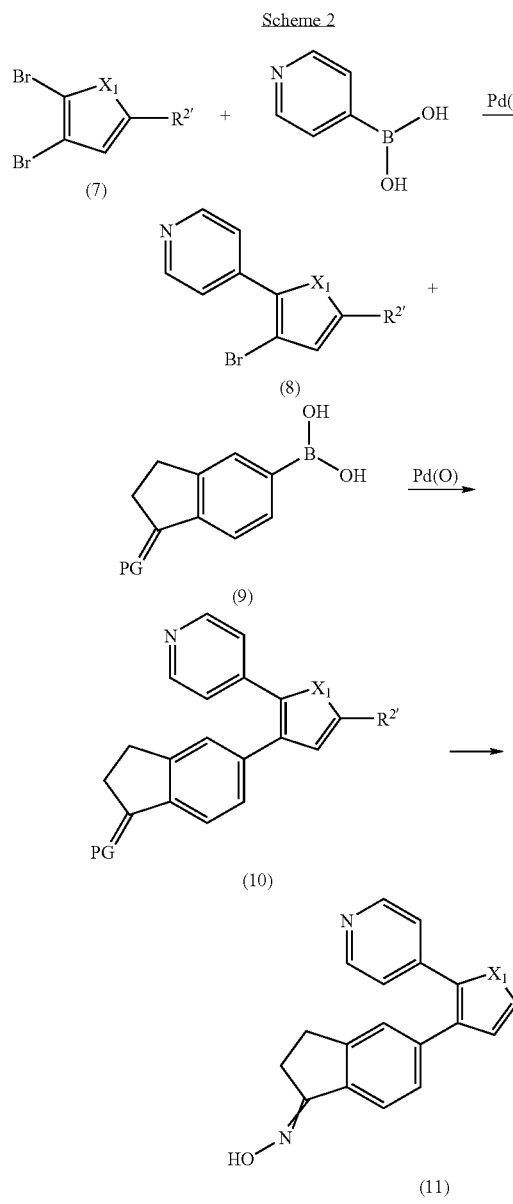

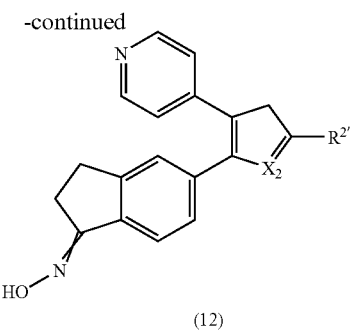

During the synthesis of the compounds of formula (I) labile functional groups in the intermediate compounds, e.g. hydroxy, carboxy and amino groups, may be protected. A comprehensive discussion of the ways in which various labile functional groups may be protected and methods for cleaving the resulting protected derivatives is given in for example *Protective Groups in Organic Chemistry*, T. W. Greene and P. G. M. Wuts, (Wiley-Interscience, New York 2nd edition, 1991).

The compounds of formula (I) may be prepared singly or as compound libraries comprising at least 2, for example 5 to 1,000 compounds, and more preferably 10 to 100 compounds of formula (I). Libraries of compounds of formula (I) may be prepared by a combinatorial 'split and mix' approach or by multiple parallel synthesis using either solution phase or solid phase chemistry, by procedures known to those skilled in the art.

Thus according to a further aspect of the invention there is provided a compound library comprising at least 2 compounds of formula (I), or pharmaceutically acceptable salts thereof.

Pharmaceutically acceptable salts may be prepared conventionally by reaction with the appropriate acid or acid derivative.

The novel aldehydes of formula (III) which are used as intermediates in the synthesis of the compounds of formula (I) also form part of the present invention:

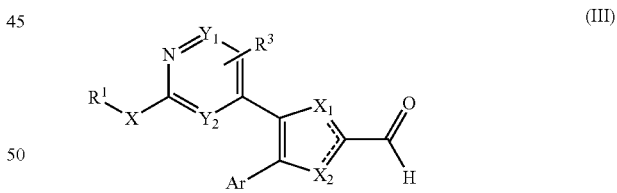

wherein X, $Y_1$, $Y_2$, $R^1$, $R^3$, Ar, $X_1$ and $X_2$ are as defined for compounds of formula (I) and R is hydrogen, $C_{1-6}$alkyl or aryl$C_{1-6}$alkyl.

As indicated above the compounds of formula (I) and their pharmaceutically acceptable derivatives are useful for the treatment and/or prophylaxis of disorders in which Raf kinases, in particular B-Raf kinase, are implicated.

According to a further aspect of the invention there is provided the use of a compound of formula (I) or a pharmaceutically acceptable salt thereof as an inhibitor of B-Raf kinase.

As indicated above the compounds of formula (I) and their pharmaceutically acceptable derivatives are useful in the treatment and/or prophylaxis of disorders associated with neuronal degeneration resulting from ischemic events, cancer, as well as chronic neurodegeneration, pain, migraine and cardiac hypertrophy.

According to a further aspect of the invention there is provided a method of treatment or prophylaxis of a neurotraumatic disease, in a mammal in need thereof, which comprises administering to said mammal an effective amount of a compound of formula (I) or a pharmaceutically acceptable derivative thereof.

According to a further aspect of the invention there is provided the use of a compound of formula (I) or a pharmaceutically acceptable derivative thereof in the manufacture of a medicament for the prophylactic or therapeutic treatment of any disease state in a human, or other mammal, which is exacerbated or caused by a neurotraumatic event.

Neurotraumatic diseases/events as defined herein include both open or penetrating head trauma, such as caused by surgery, or a closed head trauma injury, such as caused by an injury to the head region. Also included within this definition is ischemic stroke, particularly to the brain area, transient ischemic attacks following coronary by-pass and cognitive decline following other transient ischemic conditions.

Ischemic stroke may be defined as a focal neurologic disorder that results from insufficient blood supply to a particular brain area, usually as a consequence of an embolus, thrombi, or local atheromatous closure of the blood vessel. Roles for stress stimuli (such as anoxia), redox injury, excessive neuronal excitatory stimulation and inflammatory cytolines in this area has been emerging and the present invention provides a means for the potential treatment of these injuries. Relatively little treatment, for an acute injury such as these has been available.

The compounds of the invention may also be used in the treatment or prophylaxis of cancers. It is suggested that the compounds are effective in tumors that have activating B-Raf mutations (V599E) as well as tumors that are activated by Ras mutation. Mutations may occur in the Ras family members such as Kras2 with mutation G13D. Furthermore compounds of the invention may be used in the treatment or prophylaxis of colorectal cancer and melanoma.

According to a further aspect of the invention there is provided a method of treatment or prophylaxis of a mammal who is suffering from or susceptible to cancer, which comprises administering to said mammal an effective amount of a compound of formula (I) or a pharmaceutically acceptable derivative thereof.

According to a further aspect of the invention there is provided the use of a compound of formula (I) or a pharmaceutically acceptable derivative thereof in the manufacture of a medicament for the prophylactic or therapeutic treatment of cancers.

The compounds of formula (I) and pharmaceutically acceptable derivatives thereof, may be employed alone or in combination with other therapeutic agents for the treatment of the above-mentioned conditions. In particular, in anti-cancer therapy, combination with other chemotherapeutic, hormonal or antibody agents is envisaged as well as combination with surgical therapy and radiotherapy. Combination therapies according to the present invention thus comprise the administration of at least one compound of formula (I) or a pharmaceutically acceptable derivative thereof, and the use of at least one other cancer treatment method. Preferably, combination therapies according to the present invention comprise the administration of at least one compound of formula (I) or a pharmaceutically acceptable derivative thereof, and at least one other pharmaceutically active chemotherapeutic agent. These include existing and prospective chemotherapeutic agents. The compound(s) of formula (I) and the other pharmaceutically active chemotherapeutic agent(s) may be administered together in a unitary pharmaceutical composition or separately and, when administered separately this may occur simultaneously or sequentially in any order. Such sequential administration may be close in time or remote in time. The amounts of the compound(s) of formula (I) and the other pharmaceutically active chemotherapeutic agent(s) and the relative timings of administration will be selected in order to achieve the desired combined therapeutic effect.

Pharmaceutically active chemotherapeutic agents which can be useful in combination with a compound of formula (I) or a pharmaceutically acceptable derivative thereof, include but are not restricted to the following:

(1) cell cycle specific anti-neoplastic agents include, but are not limited to, diterpenoids such as paclitaxel and its analog docetaxel; tubulin poisons such as taxol/taxane or vinca alkaloids such as vinblastine, vincristine, vindesine, and vinorelbine; epipodophyllotoxins such as etoposide and teniposide; fluoropyrimidines such as 5-fluorouracil and fluorodeoxyuridine; antimetabolites such as allopurinol, fludarabine, methotrexate, cladrabine, cytarabine, mercaptopurine, gemcitabine, and thioguanine; and camptothecins such as 9-amino camptothecin, irinotecan, topotecan, and the various optical forms of 7-(4-methylpiperazino-methylene)-10,11-ethylenedioxy-20-camptothecin;

(2) cytotoxic chemotherapeutic agents including, but not limited to, alkylating agents such as melphalan, chlorambucil, cyclophosphamide, mechlorethamine, hexamethylmelamine, busulfan, carmustine, lomustine, dacarbazine and nitrosoureas; anti-tumour antibiotics such as doxorubicin, daunomycin, epirubicin, idarubicin, mitomycin-C, dacttinomycin, bleomycin and mithramycin; and platinum coordination complexes such as cisplatin, carboplatin, and oxaliplatin; and (3) other chemotherapeutic agents including, but not limited to, anti-estrogens such as tamoxifen, toremifene, raloxifene, droloxifene and iodoxyfene; progestrogens such as megestrol acetate; aromatase inhibitors such as anastrozole, letrazole, vorazole, and exemestane; antiandrogens such as flutamide, nilutamide, bicalutamide, and cyproterone acetate; LHRH agonists and antagagonists such as goserelin acetate and luprolide, testosterone 5α-dihydroreductase inhibitors such as finasteride; metalloproteinase inhibitors such as marimastat; antiprogestrogens; mitoxantrone, 1-asparaginase, urokinase plasminogen activator receptor function inhibitors; inhibitors or c-kit and bcr/abl tyrosine kinases, (such as Gleevec), immunotherapy, immunoconjugates, cytokines (such as IL-2, IFN alpha and beta), tumor vaccines (including dendritic cell vaccines), thalidomnide, COX-2 inhibitors, glucocorticoids (such as prednisone and decadron), radiation sensitizers, (such as temazolamide), growth factor function inhibitors such as inhibitors of the functions of hepatocyte growth factor; erb-B2, erb-B4, epidermal growth factor receptor (EGFR) and platelet derived growth factor receptors (PDGFR); inhibitors of angiogenesis such as inhibitors of the function of Ephrin receptors (such as, EphB4), vascular endothelial growth factor receptors (VEGFR) and the angiopoietin receptors (Tie1 and Tie2); and other kinase inhibitors such as inhibitors of CDK2 and CDK4.

Anti-neoplastic agents may induce anti-neoplastic effects in a cell-cycle specific manner, i.e., are phase specific and act at a specific phase of the cell cycle, or bind DNA and act in a non cell-cycle specific manner, i.e., are non-cell cycle specific and operate by other mechanisms.

According to a further aspect of the invention there is provided a method of treatment or prophylaxis of chronic neurodegeneration, pain, migraine or cardiac hypertrophy, in a mammal in need thereof, which comprises administering to said mammal an effective amount of a compound of formula (I) or a pharmaceutically acceptable derivative thereof.

According to a further aspect of the invention there is provided the use of a compound of formula (I) or a pharmaceutically acceptable derivative thereof in the manufacture of a medicament for the prophylactic or therapeutic treatment of chronic neurodegeneration, pain, migraine or cardiac hypertrophy.

In order to use the compounds of formula (I) in therapy, they will normally be formulated into a pharmaceutical composition in accordance with standard pharmaceutical practice.

According to a further aspect of the invention there is provided a pharmaceutical composition comprising a compound of formula (I) or a pharmaceutically acceptable derivative thereof and a pharmaceutically acceptable carrier.

The compounds of formula (I) may conveniently be administered by any of the routes conventionally used for drug administration, for instance, parenterally, orally, topically or by inhalation. The compounds of formula (I) may be administered in conventional dosage forms prepared by combining it with standard pharmaceutical carriers according to conventional procedures. The compounds of formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable carrier is dictated by the amount of compound of formula (I) with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 g. When a liquid carrier is used, the preparation will be in the form of a syrup, emulsion, soft gelatin capsule, sterile injectable liquid such as an ampoule or nonaqueous liquid suspension.

The compounds of formula (I) are preferably administered parenterally, that is by intravenous, intramuscular, subcutaneous, sublingual, intranasal, intrarectal, intravaginal or intraperitoneal administration. The intravenous form of parenteral administration is generally preferred. The compounds may be administered as a bolus or continuous infusion e.g. for 6 hours up to 3 days. Appropriate dosage forms for such administration may be prepared by conventional techniques.

The compounds of formula (I) may also be administered orally. Appropriate dosage forms for such administration may be prepared by conventional techniques.

The compounds of formula (I) may also be administered by inhalation, that is by intranasal and oral inhalation administration. Appropriate dosage forms for such administration, such as aerosol formulations, may be prepared by conventional techniques.

The compounds of formula (I) may also be administered topically, that is by non-systemic administration. This includes the application of the inhibitors externally to the epidermis or the buccal cavity and the instillation of such a compound into the ear, eye and nose, such that the compound does not significantly enter the blood stream.

For all methods of use disclosed herein the daily oral dosage regimen will preferably be from about 0.1 to about 80 mg/kg of total body weight, preferably from about 0.2 to 30 mg/kg, more preferably from about 0.5 to 15 mg/kg. The daily parenteral dosage regimen about 0.1 to about 80 mg/kg of total body weight, preferably from about 0.2 to about 30 mg/kg, and more preferably from about 0.5 to 15 mg/kg. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of the inhibitors will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of the inhibitors given per day for a defined number of days, can be ascertained by those skilled in the art using conventional course of treatment determination tests. In the case of pharmaceutically acceptable salts the above figures are calculated as the parent compound of formula (I).

No toxicological effects are indicated/expected when a compound of formula (I) is administered in the above mentioned dosage range.

All publications, including but not limited to patents and patent applications, cited in this specification are herein incorporated by reference as if each individual publication were specifically and individually indicated to be incorporated by reference herein as though fully set forth.

The following Examples illustrate the preparation of pharmacologically active compounds of the invention and the following Descriptions illustrate the preparation of intermediates used in the preparation of these compounds.

Abbreviations Used Herein are as Follows;
THF means tetrahydrofuran.
DMF means N,N-Dimethylformamide.
LDA means lithium diisopropylamide.
TBAF means tetrabutylammonium fluoride.
DMSO means methyl sulfoxide.

Description 1: 5-(2-Pyridin4-yl-furan-3-yl)-indan-1-one O-methyl oxime

Step 1. 5-Bromo-indan-1-one O-methyl oxime

A solution of 5-bromo-indan-1-one (100 g, 0.47 mol) and methoxylamine hydrochloride (56. g, 0.7 mol) in ethanol (500 ml) was treated with pyridine (57 ml, 0.7 mol). After stirring at room temperature for 30 minutes the mixture was heated at 80° C. for 3 hours. After cooling to room temperature the solution was concentrated in vacuo and the residue diluted with ethyl acetate and saturated sodium bicarbonate solution. The organic phase was washed with water and brine, dried and concentrated in vacuo to give the title compound (109 g, 96%; $^1$H NMR (CDCl$_3$) 7.52 (1H, d, J 8.3 Hz), 7.43 (1H, d, J 1 Hz), 7.35 (1H, dd, J 8.3, 1 Hz), 3.97 (3H, s), 2.99 (2H, m), 2.85 (2H, m).

Step 2. 1-Methoxyimino-indan-5-boronic acid

A solution of the product of Step 1 (48.0 g, 0.2 mol) in THF (1 L) at −78° C. under argon atmosphere was treated dropwise with n-butyl lithium (138 ml, 1.6M in hexanes, 0.22 mol). After stirring at −78° C. for 30 minutes trimethyl borate (49 ml, 0.44 mol) was added and the solution warmed to room temperature over 16 hours. The mixture was concentrated in vacuo, acidified to pH1 with 5N HCl and stirred at room temperature for 1 hour. The mixture was then basified with 40% sodium hydroxide and the solution washed three times with diethyl ether. The aqueous phase was re-acidified to pH1 and the mixture was extracted five times with ethyl acetate. The organic extracts were combined washed with brine, dried and evaporated in vacuo to give a yellow solid. The solid was triturated with hexane, filtered, washed with hexane and then a small amount of ether to give the title compound (23.6 g, 58%); MS(AP−) m/e 204 [M−H]−.

Step 3. 4-(3-Bromo-furan-2-yl)-pyridine

A degassed mixture of 2,3-dibromofuran (11.3 g, 50 mmol), 4-pyridyl boronic acid (M. Lamothe et al, *J. Med. Chem.*, 1997, 40, 3542) (6.15 g, 50 mmol) and potassium carbonate (55 g, 0.4 mol) in ethylene glycol dimethyl ether (300 ml) and water (150 ml) was treated with triphenylphosphine (1.31 g, 5 mmol) and palladium acetate (625 mg, 2.5 mmol) then heated under reflux for 18 hours. After cooling to room temperature, the mixture was filtered through filter aid and the filtrate diluted with water and ethyl acetate. The organic phase was separated, washed with water and brine, dried, concentrated in vacuo and the residue purified by silica gel chromatography to give the title compound (6.0 g, 54%); MS(ES+) m/e 224/226 [M+H]+.

Step 4. 5-(2-Pyridin-4-yl-furan-3-yl)-indan-1-one O-methyl oxime

A degassed mixture of the product of Step 3 (2.7 g, 12 mmol), the product of Step 2 (2.5 g, 12 mmol) and potassium carbonate (13.2 g, 96 mmol) in ethylene glycol dimethyl ether (70 ml) and water (30 ml) was treated with triphenylphosphine (314 mg, 1.2 mmol) and palladium acetate (135 mg, 0.6 mmol), then heated under reflux for 1 hour. After cooling to room temperature, the mixture was filtered through filter aid and the filtrate diluted with water and ethyl acetate. The organic phase was separated, washed with water and brine, dried, concentrated in vacuo and the residue purified by silica gel chromatography to give the title compound (2.9 g, 74%); MS(ES+) m/e 305 [M+H]+.

Description 2 4-(1-Methoxyimino-indan-5-yl)-5-pyridin-4-yl-furan-2-carbaldehyde A solution of the product of Description 1 (1.0 g, 3.3 mmol) in THF (10 ml) at −78° C. under argon atmosphere was treated with LDA (2 ml, 3.9 mmol, 2M solution in ethylbenzene/heptane/THF). After stirring at −78° C. for 15 minutes a solution of DMF (0.3 ml) in THF (1 ml) was added. After 15 minutes saturated ammonium chloride solution was added and the reaction mixture warmed to room temperature. The mixture was extracted with ethyl acetate and the organic phase washed with water and brine, dried and concentrated in vacuo. Purification of the residue by silica gel chromatography gave the title compound as a colourless solid (615 mg, 56%); MS(ES+) m/e 333 [M+H]+.

Description 3: 5-(1-Methoxyimino-indan-5-yl)-4-pyridin-4-yl-furan-2-carbaldehyde

Step 1. 4,5-Dibromo-furan-2-carbonyl chloride

Oxalyl chloride (10.4 ml, 0.12 mol) was added to a suspension of 4,5-dibromo-2-furoic acid (27 g, 0.1 mol) in dichloromethane (300 ml) containing dimethylformamide (0.1 ml). The mixture was stirred at room temperature for 4 h and then concentrated in vacuo. The residue was re-dissolved in dichloromethane and concentrated in vacuo; this was repeated to give the title compound which was used directly in the following step.

Step 2. 4,5-Dibromo-furan-2-carboxylic acid methoxy-methyl-amide

A solution of the product of Step 1 (0.1 mol) in dichloromethane (300 ml) was cooled to 0° C. and treated with N,O-dimethylhydroxylamine hydrochloride (11.7 g, 0.12 mol) followed by triethylamine (36 ml, 0.36 mol). The mixture was allowed to warm to room temperature and stirred for 30 minutes The solvent was evaporated in vacuo and the residue partitioned between ethyl acetate and water. After separation of the layers, the organic phase was washed sequentially with 2M hydrochloric acid, water and brine, dried and concentrated in vacuo. The product was purified by silica gel chromatography eluting with ethyl acetate/hexane (1:1) to give the title compound (30.1 g, 96%); $^1$H NMR (CDCl$_3$) 7.12 (1H, s), 3.78 (3H, s), 3.31 (3H, s).

Step 3. 4,5-Dibromo-furan-2-carbaldehyde

Diisobutylaluminum hydride (80 ml, 1M solution in toluene) was added to a solution of the product from Step 2 (20 g, 63.4 mmol) in tetrahydrofuran (160 ml) at −78° C. The mixture was stirred at −78° C. for 1.5 hours and was then quenched with a saturated aqueous solution of ammonium chloride (40 ml). The reaction was allowed to warm to room temperature, diluted with ethyl acetate and 5M hydrochloric acid (20 ml) and stirred for 30 minutes. The organic layer was separated, washed twice with water and then brine, dried and concentrated in vacuo to yield the title compound (12.9 g, 81%); $^1$H NMR (CDCl$_3$) 9.52 (1H, s), 7.21 (1H, s).

Step 4. 4-Bromo-5-(1-methoxyimino-indan-5-yl)-furan-2-carbaldehyde

A degassed mixture of the product of Step 3 (6.6 g, 26.0 mmol), 1-methoxyimino-indan-5-boronic acid (5.3 g, 26.0 mmol) and potassium carbonate (28 g, 202 mmol) in ethylene glycol dimethyl ether (150 ml) and water (75 ml) was treated with bis(triphenylphosphine) palladium (II) chloride (1.05 g, 1.5 mmol), then heated under reflux for 6 hours. After cooling to room temperature, the mixture was filtered through celite and the filtrate diluted with water and ethyl acetate. The organic phase was separated, washed with water and brine, dried, concentrated in vacuo and the residue purified by silica gel chromatography eluting with dichloromethane to give the title compound (3.06 g, 35%); MS(ES+) m/e 334/336 [M+H]$^+$.

Step 5. 5-(1-Methoxyimino-indan-5-yl)-4-pyridin-4-yl-furan-2-carbaldehyde

A degassed mixture of the product of Step 4 (2.0 g, 6.0 mmol) and 4-tributylstannylpyridine (2.5 g, 6.8 mmol) in toluene (100 ml) was treated with triphenylphosphine (156 mg, 0.6 mmol) and palladium acetate (67 mg, 0.3 mmol) then heated under reflux for 60 hours. The reaction mixture was concentrated in vacuo and the product purified by silica gel chromatography eluting with ethyl acetate/hexane (1:1) and then ethyl acetate to give the title compound (1.37 g, 69%); MS(ES+) m/e 333 [M+H]$^+$.

EXAMPLE 1

5-(5-Morpholin-4-ylmethyl-2-pyridin-4-yl-furan-3-yl)-indan-1-one oxime

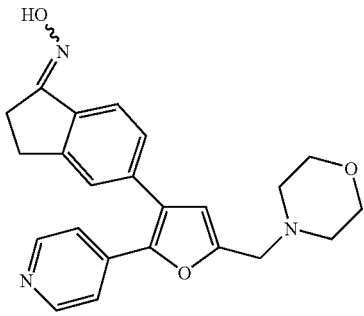

Step 1. 5-(5-Morpholin-4-ylmethyl-2-pyridin-4-yl-furan-3-yl)-indan-1-one O-methyl-oxime A mixture of the product of Description 2 (156 mg, 9 mmol), morpholine (53 mg, 0.6 mmol) and polymer bound trimethylammonium cyanoborohydride (250 mg, 1 mmol, 4 mmol/g) in methanol (5 ml) containing acetic acid (0.2 ml) was stirred at room temperature for 24 hours. The reaction mixture was then filtered and the resin washed with methanol. The filtrate was concentrated in vacuo. The residue was purified by silica gel chromatography eluting with a 0.1:1:25 mixture of 0.880 ammonia solution:ethanol:chloroform to give the title compound (162 mg, 61%) as a solid; MS(AP+) m/e 404 [M+H]+.

Step 2. 5-(4-Morpholin-4-ylmethyl-2-pyridin-4-yl-furan-3-yl)-indan-1-one

A mixture of the product of Step 1 (162 mg, 0.41 mmol) and 5M HCl (1 ml) in dioxane (2 ml)/acetone (5 ml) was heated at 100° C. for 2 hour. The mixture was then cooled to room temperature and the solvent evaporated in vacuo. The residue was co-evaporated with acetone (2×20 ml) and ethanol/acetone (1:1, 20 ml) to give the title compound (180 mg) as the dihydrochloride salt which was used directly in the next step; MS(ES+) m/e 375 [M+H]+.

Step 3. 5-(5-Morpholin-4-ylmethyl-2-pyridin-4-yl-furan-3-yl)-indan-1-one oxime

The product of Step 2 (180 mg, 0.4 mmol) in ethanol (4 ml) containing aqueous hydroxylamine (2 ml, 50% in water) was heated under reflux for 1 hour. After cooling to room temperature, the mixture was concentrated in vacuo and the residue co-evaporated with ethanol (3×5 ml). The residue was purified by silica gel chromatography eluting with a 0.1:1:20 mixture of 0.880 ammonia solution:ethanol:chloroform to give the title compound (100 mg, 64%); MS(ES+) m/e 390 [M+H]+.

The following examples were prepared from the product of Description 2 by the general three-step method described in Example 1.

| | Example | Amine | Characterisation |
|---|---|---|---|
| 2 | 5-(5-Piperidin-1-ylmethyl-2-pyridin-4-yl-furan-3-yl)-indan-1-one oxime | Piperidine | MS(ES+) m/e 388 [M + H]+ |
| 3 | 5-(2-Pyridin-4-yl-5-pyrrolidin-1-ylmethyl-furan-3-yl)-indan-1-one oxime | Pyrrolidine | MS(ES+) m/e 374 [M + H]+ |
| 4 | 5-{5-(4-Methyl-piperazin-1-ylmethyl)-2-pyridin-4-yl-furan-3-yl]-indan-1-one oxime | 4-Methylpiperazine | MS(ES+) m/e 403 [M + H]+ |
| 5 | 5-[5-(1,1-Dioxo-1-thiomorpholin-4-ylmethyl)-2-pyridin-4-yl-furan-3-yl]-indan-1-one oxime | Thiomorpholine-1,1-dioxide | MS(ES+) m/e 438 [M + H]+ |
| 6 | 5-(5-Piperazin-1-ylmethyl-2-pyridin-4-yl-furan-3-yl)-indan-1-one oxime | Piperazine-1-carboxylic acid tert-butyl ester | MS(ES+) m/e 389 [M + H]+ |
| 7 | 5-(5-Dimethylaminomethyl-2-pyridin-4-yl-furan-3-yl)-indan-1-one oxime | Dimethylamine | MS(ES+) m/e 348 [M + H]+ |
| 8 | 5-{5-[(2-Methoxyethylamino)-methyl]-2-pyridin-4-yl-furan-3-yl}-indan-1-one oxime | 2-Methoxyethylamine | MS(ES+) m/e 378 [M + H]+ |

EXAMPLE 9

5-(5-{[1-(2-Methoxy-ethyl)-piperidin-4-ylamino]-methyl}-3-pyridin-4-yl-furan-2-yl)-indan-1-one oxime

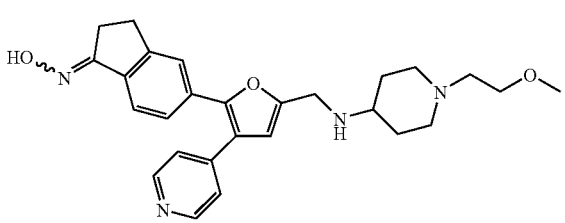

Step 1. [1-(2-Methoxy-ethyl)-piperidin-4-yl]-carbamic acid tert-butyl ester

A solution of 4-amino-1-N-tert-butyloxycarbonyl-piperidine (3.0 g, 15.0 mmol) in ethanol (20 ml) was treated with potassium carbonate (3.7 g, 26.8 mmol) and 2-bromoethyl methyl ether (2.3 g, 16.5 mmol). The reaction mixture was heated to reflux for 24 hours, cooled and then filtered. The filtrate was concentrated in vacuo and the residue purified by silica gel chromatography eluting with chloroform/ethanol/0.880 ammonia solution (95:4.5:0.5) to yield the title compound (2.02 g, 52%); $^1$H NMR (CD$_3$OD) 4.04 (2H, m), 3.49 (2H, t, J 5.2 Hz), 3.31 (3H, s), 2.76 (2H, t, J 5.2 Hz), 2.62 (3H, m), 1.88 (2H, m), 1.44 (9H, s), 1.19 (2H, m).

Step 2: 1-(2-Methoxy-ethyl)-piperidin4-ylamine

A solution of the product from Step 1 (500 mg, 1.94 mmol) in dichloromethane (5 ml) was cooled to 0° C. and treated with trifluoroacetic acid (2 ml). The mixture was allowed to warm to room temperature and stirred for a further 1 hour. After evaporation of the solvent in vacuo, the residue was partitioned between dichloromethane and an aqueous solution of sodium carbonate. After separation of the layers the aqueous phase was re-extracted six times with dichloromethane, dried and concentrated in vacuo to yield the title compound (145 mg, 47%); $^1$H NMR (CD$_3$OD) 3.49 (2H, t, J 5.2 Hz), 3.35 (3H, s), 3.30 (2H, m), 3.10 (1H, s), 2.80 (2H, t, J 5.2 Hz), 2.68 (2H, m), 1.91 (2H, m), 1.30 (2H, m).

Step 3. 5-(5-{[1-(2-Methoxy-ethyl)-piperidin-4-ylamino]-methyl}-3-pyridin-4-yl-furan-2-yl)-indan-1-one O-methyloxime The title compound was prepared from the product of Step 2 and the product of Description 3 as described in Example 1 Step 1; MS(ES+) m/e 476 [M+H]$^+$.

Step 4. 5-(5-{[1-(2-Methoxy-ethyl)-piperidin-4-ylamino]-methyl}-3-pyridin-4-yl-furan-2-yl)-indan-1-one The title compound was prepared from the product of Step 3 as described in Example 1 Step 2; MS(ES+) m/e 446 [M+H]$^+$.

Step 5. 5-(5-{[1-(2-Methoxy-ethyl)-piperdin-4-ylamino]-methyl}-3-pyridin-4-yl-furan-2-yl)-indan-1-one oxime The title compound was prepared from the product of Step 4 as described in Example 1 Step 3; MS(ES+) m/e 461 [M+H]$^+$.

The following examples were prepared from the product of Description 3 using the general three-step method described in Example 1.

| Example | | Amine | Characterisation |
|---|---|---|---|
| 10 | 5-(5-Morpholin-4-ylmethyl-3-pyridin-4-yl-furan-2-yl)-indan-1-one oxime | Morpholine | MS(ES+) m/e 390 [M + H]$^+$ |
| 11 | 5-(5-Piperidin-1-ylmethyl-3-pyridin-4-yl-furan-2-yl)-indan-1-one oxime | Piperidine | MS(ES+) m/e 388 [M + H]$^+$ |
| 12 | 5-[3-Pyridin-4-yl-5-(4-pyrrolidin-1-yl-piperidin-1-ylmethyl)-furan-2-yl]-indan-1-one oxime | 4-Pyrrolidin-1-yl-piperidine | MS(ES+) m/e 457 [M + H]$^+$ |
| 13 | 5-{5-[(2-Methoxy-ethylamino)-methyl]-3-pyridin-4-yl-furan-2-yl}-indan-1-one oxime | 2-Methoxy-ethylamine | MS(ES+) m/e 378 [M + H]$^+$ |
| 14 | 5-(5-Diethylaminomethyl-3-pyridin-4-yl-furan-2-yl)-indan-1-one oxime | Diethylamine | MS(ES+) m/e 376 [M + H]$^+$ |
| 15 | 5-[5-(4-Ethyl-piperazin-1-ylmethyl)-3-pyridin-4-yl-furan-2-yl]-indan-1-one oxime | 1-Ethyl-piperazine | MS(ES+) m/e 417 [M + H]$^+$ |
| 16 | 5-{5-[4-(2-Methoxy-ethyl)-piperazin-1-ylmethyl]-3-pyridin-4-yl-furan-2-yl}-indan-1-one oxime | 1-(2-Methoxy-ethyl)-piperazine | MS(ES+) m/e 447 [M + H]$^+$ |
| 17 | 5-{5-[(2-Morpholin-4-yl-ethylamino)-methyl]-3-pyridin-4-yl-furan-2-yl}-indan-1-one oxime | 2-Morpholin-4-yl-ethylamine | MS(ES+) m/e 433 [M + H]$^+$ |
| 18 | 5-(5-{[Methyl-(1-methyl-piperidin-4-yl)-amino]-methyl}-3-pyridin-4-yl-furan-2-yl)-indan-1-one oxime | Methyl-(1-methyl-piperidin-4-yl)-amine | MS(ES+) m/e 431 [M + H]$^+$ |
| 19 | 5-[5-(4-Methyl-piperazin-1-ylmethyl)-3-pyridin-4-yl-furan-2-yl]-indan-1-one oxime | 1-Methyl-piperazine | MS(ES+) m/e 403 [M + H]$^+$ |
| 20 | 5-(3-Pyridin-4-yl-5-pyrrolidin-1-ylmethyl-furan-2-yl)-indan-1-one oxime | Pyrrolidine | MS(ES+) m/e 374 [M + H]$^+$ |
| 21 | 5-(5-Dimethylaminomethyl-3-pyridin-4-yl-furan-2-yl)-indan-1-one oxime | Dimethylamine | MS(ES+) m/e 348 [M + H]$^+$ |
| 22 | 5-{5-[4-(2-Hydroxy-ethyl)-piperazin-1-ylmethyl]-3-pyridin-4-yl-furan-2-yl}-indan-1-one oxime | 2-Piperazin-1-yl-ethanol | MS(ES+) m/e 433 [M + H]$^+$ |
| 23 | 5-(5-{[(2-Methoxy-ethyl)-methyl-amino]-methyl}-3-pyridin-4-yl-furan-2-yl)-indan-1-one oxime | (2-Methoxy-ethyl)-methyl-amine | MS(ES+) m/e 392 [M + H]$^+$ |
| 24 | 5-(5-{[Isopropyl-(2-methoxy-ethyl)-amino]-methyl}-3-pyridin-4-yl-furan-2-yl)-indan-1-one oxime | Isopropyl-(2-methoxy-ethyl)-amine | MS(ES+) m/e 420 [M + H]$^+$ |
| 25 | 5-[5-(1,1-Dioxo-1-thiomorpholin-4-ylmethyl)-3-pyridin-4-yl-furan-2-yl]-indan-1-one oxime | Thiomorpholine 1,1-dioxide | MS(ES+) m/e 439 [M + H]$^+$ |
| 26 | 5-(5-Piperazin-1-ylmethyl-3-pyridin-4-yl-furan-2-yl)-indan-1-one oxime | Piperazine-1-carboxylic acid tert-buty ester | MS(ES+) m/e 389 [M + H]$^+$ |

EXAMPLE 27

5-(5-Piperidin-1-ylmethyl-2-pyrimidin-4-yl-furan-3-yl)-indan-1-one oxime

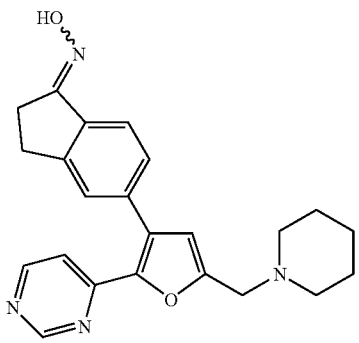

Step 1. 1-(4,5-Dibromo-furan-2-ylmethyl)-piperidine

The title compound (1.15 g, 68%) was prepared from the product of Description 3 Step 3 (1.33 g, 5.23 mmol) and piperidine (0.534 g, 6.28 mmol) as described in Example 1 Step 1; MS(ES+) m/e 322/324/326 [M+H]$^+$.

Step 2. 4-(3-Bromo-5-piperidin-1-ylmethyl-furan-2-yl)-2-methylsulfanyl-pyrimidine Bis(triphenylphosphine)palladium(II) chloride (0.226 g, 0.323 mmol) was added to a solution of the product of Step 1 (1.15 g, 3.56 mmol) in dry toluene (10 ml). 2-Methylsulfanyl-4-trimethylstannanyl-pyrimidine (K. Undheim et al, Tetrahedron, 1994, 50(1), 275) (0.939 g, 3.23 mmol) was added to this solution and the reaction was then heated at 100° C. for 18 hours. After cooling to room temperature the solvent was removed in vacuo and the residue purified by chromatography on silica gel eluting with a mixture of 0.880 ammonia/methanol/dichloromethane (0.3:2.7:97) to furnish the title compound (0.220 g, 0.597 mmol); MS(ES+) m/e 370/372 [M+H]$^+$.

Step 3. 5-[2-(2-Methylsulfanyl-pyrimidin-4-yl)-5-piperidin-1-ylmethyl-furan-3-yl]-indan-1-one O-methyl-oxime A mixture of the products from Step 2 (0.6 g, 1.62 mmol) and Description 1 Step 2 (0.367 g, 1.8 mmol) in toluene (10 ml) was treated with bis(triphenylphosphine) palladium (II) chloride (0.113 g, 0.162 mmol) and 2M aqueous sodium carbonate (0.2 ml, 3.93 mmol) and heated under reflux for 18 hours. After cooling to room temperature, the mixture was poured into ethyl acetate, washed with saturated aqueous sodium bicarbonate solution and brine, dried and reduced in vacuo. The crude title compound (0.310 g) was used in the next step without further purification; MS(ES+) m/e 449 [M+H]$^+$.

Step 4. 5-[2-(2-Methylsulfanyl-pyrimidin-4-yl)-5-piperidin-1-ylmethyl-furan-3-yl]-indan-1-one A mixture of the product from Step 3 (0.310 g, 0.692 mmol) and 5M HCl (3 ml) in dioxane (3 ml)/acetone (1 ml) was heated at 100° C. for 1 hour. The mixture was then cooled to room temperature and poured into ethyl acetate and washed with saturated aqueous sodium bicarbonate solution. The ethyl acetate was then dried and the solvent evaporated in vacuo and the residue chromatographed on silica gel eluting with a mixture of 0.880 ammonia/methanol/dichloromethane (0.5:4.5:95) to furnish the title compound (0.145 g, 0.345 mmol); MS(ES+) m/e 420 [M+H]$^+$.

Step 5. 5-(5-Piperidin-1-ylmethyl-2-pyrimidin-4-yl-furan-3-yl)-indan-1-one

A mixture of the product of Step 4 (0.135 g, 0.329 mmol) and Raney nickel (0.262 g of an aqueous suspension) in ethanol (15 ml) and water (5 ml) was heated at 100° C. for 20 hours. The mixture was then cooled to room temperature, filtered through celite and the filtrate reduced in vacuo. The residue was then purified by chromatography on silica gel eluting with a mixture of 0.880 ammonia/methanol/dichloromethane (0.5:4.5:95), to furnish the title compound (0.016 g, 0.345 mmol); MS(ES+) m/e 374 [M+H]$^+$.

Step 6. 5-(5-Piperidin-1-ylmethyl-2-pyrimidin-4-yl-furan-3-yl)-indan-1-one oxime The title compound (0.016 g, 0.041 mmol) was prepared from the product of Step 5 as described in Example 1 Step 3; MS(ES+) m/e 389 [M+H]$^+$.

EXAMPLE 28

5-[2-(2-Amino-pyrimidin-4-yl)-5-piperidin-1-ylmethyl-furan-3-yl]-indan-1-one oxime

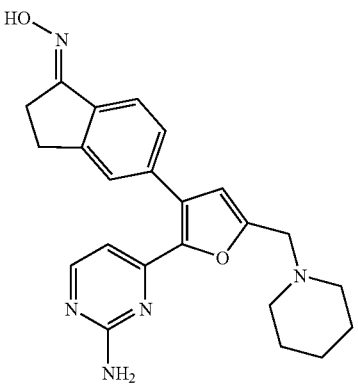

Step 1. 5-[2-(2-Methanesulfonyl-pyrimidin-4-y)-5-piperidin-1-ylmethyl-furan-3-yl]-indan-1-one 30% Hydrogen peroxide (0.138 g, 1.22 mmol) followed by sodium tungstate (0.0067 g, 0.0203 mmol) was added to a suspension of the product from Example 27 Step 4 (0.170 g, 0.405 mmol) in HCl (5.4 ml, 0.81 mmol, 0.15M). The mixture was stirred overnight at room temperature before being poured into water and treated with saturated aqueous sodium thiosulphate solution. The aqueous mixture was then neutralised with saturated aqueous sodium bicarbonate solution and then extracted several times with dichoromethane. The organic extracts were then dried with sodium sulphate, filtered and reduced in vacuo. The resulting yellow solid residue (0.150 g) was used directly in the next step without further purification; MS(ES+) m/e 452 [M+H]$^+$.

Step 2. 5-[2-(2-Amino-pyrimidin-4-yl)-5-piperidin-1-ylmethyl-furan-3-yl]-indan-1-one 0.880 Ammonia solution (5 ml) was added to the residue from Step 1 (0.045 g, 0.1 mmol) in THF (1 ml). The reaction mixture was then heated at 100° C. in an autoclave for 18 hours and then cooled to 0° C. and extracted with chloroform. The organic extracts were then dried with sodium sulphate, filtered and reduced in vacuo. The residue was purified by chromatography on silica gel eluting with a mixture of 0.880 ammonia/methanol/chloroform (0.6:5.4:94) to furnish the title compound (0.013 g, 0.036 mmol); MS(ES+) m/e 389 [M+H]$^+$.

Step 3. 5-[2-(2-Amino-pyrimidin-4-yl)-5-piperidin-1-ylmethyl-furan-3-yl]-indan-1-one oxime The title compound (0.010 g, 0.025 mmol) was prepared from the product of Step 2 (0.011 g, 0.028 mmol) as described in Example 1 Step 3; MS(ES+) m/e 405 [M+H]+.

EXAMPLE 29

5-[5-(4-Hydroxy-piperidin-4-yl)-2-pyridin-4-yl-furan-3-yl]-indan-1-one oxime

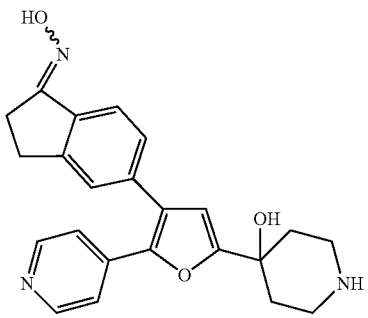

Step 1. 4-Hydroxy-4-[4-(1-methoxyimino-indan-5-yl)-5-pyridin-4-yl-furan-2-yl]-piperidine-1-carboxylic acid tert butyl ester A solution of the product of Description 1 (840 mg, 2.75 mmol) in THF (15 ml) at −78° C. under argon atmosphere was treated with LDA (1.65 ml, 3.3 mmol, 2M solution in ethylbenzene/heptane/THF). After stirring at −78° C. for 15 minutes a solution of 4-oxo-piperidine-1-carboxylic acid tert butyl ester (550 mg, 2.75 mmol) in THF (4 ml) was added over 15 minutes and the reaction mixture was allowed to warm to room temperature over 18 hours. Saturated ammonium chloride solution was then added and the mixture extracted with ethyl acetate and the organic phase washed with water and brine, dried and concentrated in vacuo. Purification of the residue by silica gel chromatography gave the title compound (618 mg, 45%); MS(ES+) m/e 504 [M+H]+.

Step 2. 5-[5-(4-Hydroxy-piperidin-4-yl)-2-pyridin-4-yl-furan-3-yl]-indan-1-one

A mixture of the product of Step 1 (350 mg, 0.7 mmol) and 5M HCl (3 ml) in dioxane (3 ml)/acetone (10 ml) was heated at 100° C. for 4 hour. The mixture was then cooled to room temperature and the solvent evaporated in vacuo. The residue was co-evaporated with acetone (2×2 ml) and ethanol/acetone (1:1, 20 ml) to give the title compound as the dihydrochloride salt which was used directly in the next step; MS(ES+) m/e 375 [M+H]+.

Step 3. 5-[5-(4-Hydroxy-piperidin-4-yl)-2-pyridin-4-yl-furan-3-yl]-indan-1-one oxime The product of Step 2 (200 mg, 0.54 mmol) in ethanol (4 ml) containing aqueous hydroxylamine (2 ml, 50% in water) was heated under reflux for 1 hour. After cooling to room temperature, the mixture was concentrated in vacuo and the residue co-evaporated with ethanol (3×5 ml). The residue was purified by silica gel chromatography eluting with a 1:9:90 mixture of 0.880 ammonia solution:ethanol:chloroform to give the title compound (86 mg, 40%); MS(ES+) m/e 390 [M+H]+.

EXAMPLE 30

5-[2-Pyridin-4-yl-5-(1,2,3,6-tetrahydro-pyridin-4-yl)-furan-3-yl]-indan-1-one oxime

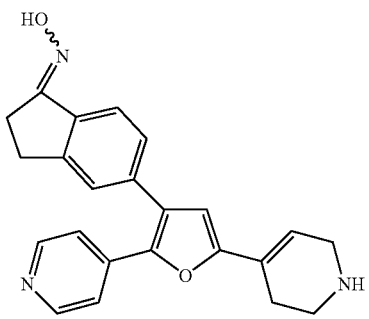

Step 1. 4-[-4-(1-Methoxyimino-indan-5-yl)-5-pyridin-4-yl-furan-2-yl]-3,6-dihydro-2H-pyridine-1-carboxylic acid tert butyl ester A solution of the product of Example 29, Step 1 (1.06 g, 2.0 mmol) in THF (25 ml) at 0° C. was treated with (methoxycarbonylsulfamoyl)-triethylammonium hydroxide inner salt (Burgess reagent, 952 mg, 4 mmol). After 18 hours at room temperature the mixture was diluted with ethyl acetate and water. The organic phase was washed with water and brine, dried and concentrated in vacuo. Purification of the residue by silica gel chromatography gave the title compound (450 mg, 46%); MS(ES+) m/e 486 [M+H]+.

Step 2. 5-[2-Pyridin-4-yl-5-(1,2,3,6-tetrahydro-pyridin-4-yl)-furan-3-yl]-indan-1-one oxime The title compound was prepared from the product of Step 1 using the methods described in Example 1, Steps 2 and 3; MS(ES+) m/e 372 [M+H]+.

EXAMPLE 31

5-(5-Piperidin-4-yl-2-pyridin-4-yl-furan-3-yl)-indan-1-one oxime

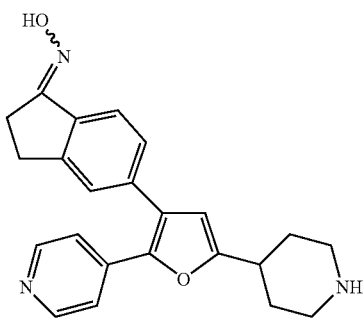

Step 1. 1-Methoxyimino-indan-5-carbaldehyde

A solution of the product of Description 1 (112 g, 0.46 mol) in THF (1500 ml) at −60° C. under argon was treated with n-BuLi (325 ml, 1.6M in hexanes, 0.52 mol) over 1 hour.

After stirring at −60° C. for 1 hour a solution of DMF (39.7 ml) in THF (50 ml) was added dropwise over 1 hour. The reaction was stirred at −60° C. for a further 1 hour before being allowed to warm to room temperature. The reaction was quenched with saturated aqueous sodium hydrogen carbonate solution and extracted into ethyl acetate. The organic phase was separated, dried, concentrated in vacuo and the residue purified by silica gel chromatography to give the title compound (57 g, 65%); $^1$H NMR (CDCl$_3$) 10.0(1H,s), 7.83-7.73 (3H, m), 4.02 (3H, s), 3.10 (2H, m), 2.92 (2H, m).

Step 2. 4-[(E)-3-(1-Methoxyimino-indan-5-yl)-allanoyl]-piperidine-1-carboxylic acid benzyl ester A mixture of the product of Step 1 (4.8 g, 25 mmol), sodium methoxide (1.35 g, 25 mmol) and 4-acetyl-piperidine-1-carboxylic acid benzyl ester (6.4 g, 25 mmol) (WO97/05877) in methanol (100 ml) was heated at reflux for 8 hours. After cooling to room temperature the solution was concentrated in vacuo and the residue diluted with ethyl acetate and water. The organic phase was washed with water and brine, dried and concentrated in vacuo and the residue purified by silica gel chromatography to give the title compound (6.92 g, 64%); MS(ES+) m/e 433 [M+H]+.

Step 3. 4-[3-(1-Methoxyimino-indan-5-yl)-4oxo-4-pyridin-4-yl-butanoyl]-piperidine-1-carboxylic acid benzyl ester A solution of sodium cyanide (240 mg, 4.8 mmol) in DMF (15 ml) was treated with a solution of pyridine-4-carbaldehyde (1.71 g, 16 mmol) in DMF (25 ml). After 15 minutes a solution of the product of Step 2 (6.92 g, 16 mmol) in DMF (20 ml) was added dropwise. After stirring at room temperature for 18 hours the mixture was diluted with saturated sodium bicarbonate solution and ethyl acetate. The organic phase was washed with water and brine, dried and concentrated in vacuo and the residue purified by silica gel chromatography to give the title compound (5.6 g, 65%); MS(ES+) m/e 540 [M+H]+.

Step 4. 5-(5-Piperidin-4-yl-2-pyridin-4-yl-furan-3-yl)-indan-1-one O-methyl-oxime The product of Step 3 (3.0 g, 5.5 mmol) was added to a stirred suspension of phosphorus pentoxide (8 g) in dry methane sulphonic acid (50 ml). After stirring at room temperature for 4 hours the reaction mixture was cautiously poured into a stirred solution of ice cold 50% aqueous sodium hydroxide (final pH 10). The mixture was extracted with chloroform, washed with water and brine, dried and concentrated in vacuo and the residue purified by silica gel chromatography to give the title compound (0.66 g, 32%); MS(ES+) m/e 388 [M+H]+.

Step 5. 5-(5-Piperidin4-yl-2-pyridin-4-yl-furan-3-yl)-indan-1-one

The title compound was prepared from the product of Step 4 using the method described in Example 1 Step 2; MS(ES+) m/e 359 [M+H]+.

Step 6. 5-(5-Piperidin-4-yl-2-pyridin-4-yl-furan-3-yl)-indan-1-one oxime

The title compound was prepared from the product of Step 5 using the method described in Example 1 Step 3; MS(ES+) m/e 374 [M+H]+.

EXAMPLE 32

5-{5-[1-(2-Methoxyethyl)-piperidin-4-yl]-2-pyridin-4-yl-furan-3-yl}-indan-1-one oxime

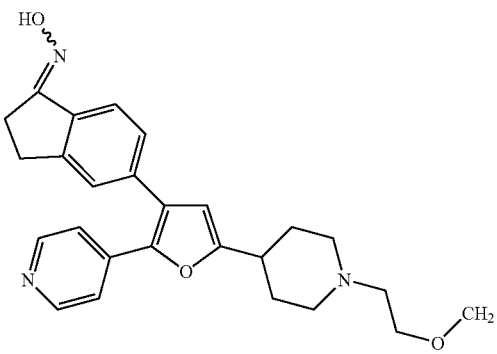

A mixture of the product of Example 31 (0.149 g, 0.4 mmol), methoxy-acetaldehyde (0.037 g, 0.5 mmol) (E. M. Acton et al, *J. Med. Chem.*, 1986, 29, 2074) and polymer bound trimethylammonium cyanoborohydride (200 mg, 0.8 mmol, 4 mmol/g) in methanol (5 ml) containing acetic acid (0.2 ml) was stirred at room temperature for 24 hours. The reaction mixture was then filtered and the resin washed with methanol. The filtrate was concentrated in vacuo and the residue purified by silica gel chromatography eluting with a 1:9:90 mixture of 0.880 ammonia solution:ethanol:chloroform to give the title compound (0.103 g, 60%); MS(ES+) m/e 432 [M+H]+.

EXAMPLE 33

5-(5-{1-[2-(4-Chloro-phenoxy)-ethyl]-piperidin-4-yl}-2-pyridin-4-yl-furan-3-yl)-indan-1-one oxime

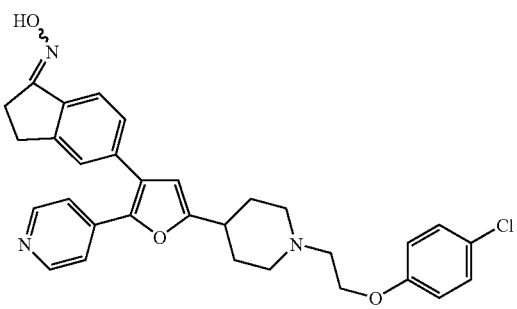

Step 1: 5-(5-{1-[2-(4-Chloro-phenoxy)-ethyl]-piperidin-4-yl}-2-pyridin-4-yl-furan-3-yl)-indan-1-one The title compound (0.140 g, 65%) was prepared from the product of Example 31 Step 5 and (4-chlorophenoxy)acetaldehyde (Maguire et al, *J. Chem. Soc.*, 1954, 3669) using the method of Example 32; MS(ES+) m/e 513 [M+H]+.

Step 2: 5-(5-{1-[2-(4-Chloro-phenoxy)-ethyl]-piperidin-4-yl}-2-pyridin-4-yl-furan-3-yl)-indan-1-one oxime The title compound (0.115 g, 88%) was prepared from the product of Step 1 using the method of Example 1 Step 3; MS(ES+) m/e 528 [M+H]⁺.

The following examples were prepared from the product of Example 31 Step 5 by the general two step method described in Example 33, Steps 1 and 2.

| Example | Aldehyde/Ketone | Characterisation |
|---|---|---|
| 34 5-[5-(1-Cyclopentyl-piperidin-4-yl)-2-pyridin-4-yl-furan-3-yl]-indan-1-one oxime | Cyclopentanone | MS(ES+) m/e 442 [M + H]⁺ |
| 35 5-[5-(1-Cyclopropylmethyl-piperidin-4-yl)-2-pyridin-4-yl-furan-3-yl]-indan-1-one oxime | Cyclopropanecarbaldehyde | MS(ES+) m/e 428 [M + H]⁺ |
| 36 5-{5-[1-(2-Morpholin-4-yl-ethyl)-piperidin-4-yl]-2-pyridin-4-yl-furan-3-yl}-indan-1-one oxime | Morpholin-4-yl-acetaldehyde (L. Duhamel et al., Bull. Soc. Chim. Fr., 1968, 11, 4423) | MS(ES+) m/e 487 [M + H]⁺ |

EXAMPLE 37

5-[5-(1-Methanesulfonyl-piperidin-4-yl)-2-pyridin-4-yl-furan-3-yl]-indan-1-one oxime

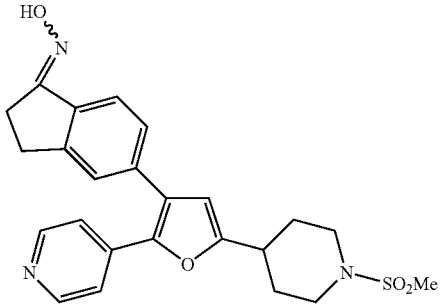

Step 1. 5-[5-(1-Methanesulfonyl-piperidin4-yl)-2-pyridin-4-yl-furan-3-yl]-indan-1-one O-methyl-oxime The product of Example 31, Step 3 (3.0 g, 5.5 mmol) was added to a stirred suspension of phosphorus pentoxide (8 g) in dry methane sulphonic acid (50 ml). After stirring at room temperature for 4 hours the reaction mixture was cautiously poured into a stirred solution of ice cold 50% aqueous sodium hydroxide (final pH 10). The mixture was extracted with chloroform, washed with water and brine, dried and concentrated in vacuo and the residue purified by silica gel chromatography to give the title compound (1.04 g, 50%); MS(ES+) m/e 466 [M+H]+.

Step 2: 5-[5-(1-Methanesulfonyl-piperidin-4-yl)-2-pyridin-4-yl-furan-3-yl]-indan-1-one oxime The title compound was prepared from the product of Step 1 using the methods described in Example 1 Steps 2 and 3; MS(ES+) m/e 452 [M+H]+.

EXAMPLE 38

5-{5-[1-(2-Dimethylamino-ethanoyl)-piperidin-4-yl]-2-pyridin-4-yl-furan-3-yl}-indan-1-one oxime

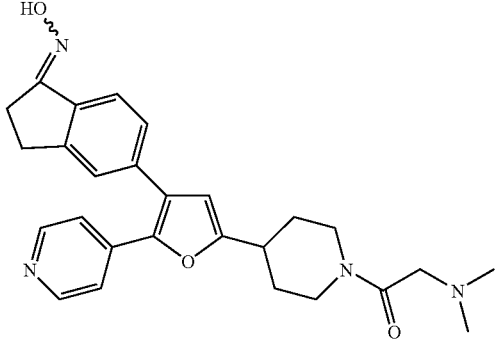

Step 1. 5-{5-[1-(2-Dimethylamino-ethanoyl)-piperidin-4-yl]-2-pyridin-4-yl-furan-3-yl}-indan-1-one A mixture of the product from Example 31 Step 5 (0.17 g, 0.47 mmol), N-cyclohexylcarbodiimide,N'-methyl polystyrene resin (0.4 g, 0.65 mmol, 1.7 mmol/g), and 1-hydroxybenzotriazole hydrate (0.081 g, 0.6 mmol) were suspended in DMF (4 ml) and treated with triethylamine (0.084 ml, 0.6 mmol) and dimethylamino-acetic acid (0.048 g, 0.47 mmol). The reaction was stirred at room temperature for 16 hours and filtered on to a 10 g SCX cartridge (Varian Mega Bond Elute). The cartridge was then washed with methanol and then a 1:90.880 ammonia:methanol solution. The ammonia containing fractions were then reduced in vacuo and the residue purified by chromatography on silica gel eluting with a mixture of 0.880 ammonia/methanol/chloroform (0.5:4.5:95) to afford the title compound (0.097 g, 47%); MS (ES+) m/e 444 (M+H)⁺.

Step 2. 5-{5-[1-(2-Dimethylamino-ethanoyl)-piperidin-4-yl]-2-pyridin-4-yl-furan-3-yl}-indan-1-one oxime The title compound (0.053 g, 63%) was prepared from the product of Step 1 using the method of Example 1 Step 3; MS(ES+) m/e 459 [M+H]⁺.

The following example was prepared from the product of Example 31 Step 5 by the general two step method described in Example 38.

adjusted to pH 11. The suspension was filtered through Celite and the filter pad washed with water and chloroform. The filter pad was then washed with methanol and the filtrate concentrated in vacuo and the residue purified by silica gel chromatography eluting with a 1:10:40 mixture of 0.880 ammonia solution:ethanol:chloroform to give the title compound (523 mg, 42%); MS(ES+) m/e 388 [M+H]⁺.

| Example | Acid | Characterisation |
|---|---|---|
| 39 5-{5-[1-(3-Piperidin-1-yl-propanoyl)-piperidin-4-yl]-2-pyridin-4-yl-furan-3-yl}-indan-1-one oxime | 3-Piperidin-1-yl-propionic acid | MS(ES+) m/e 513 [M + H]⁺ |

EXAMPLE 40

5-(5-Piperidin-4-yl-3-pyridin-4-yl-furan-2-yl)-indan-1-one oxime

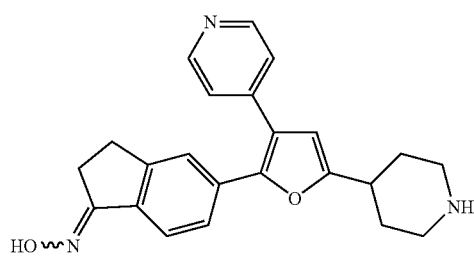

Step 1. 4-[(E)-3-Pyridin-4-yl-allanoyl]-piperidine-1-carboxylic acid benzyl ester A solution of dry pyridine (8 ml) and pyridine-4-carboxaldehyde (3.75 g, 35 mmol) was treated with 4-acetyl-piperidine1-carboxylic acid benzyl ester (9.1 g, 35 mmol) and diethylamine (3.9 ml, 35 mmol). The solution was heated under reflux for 18 hours, cooled to room temperature and poured into ice water containing concentrated hydrochloric acid. The resulting solution was adjusted to pH 9 by addition of sodium hydroxide solution, the mixture was extracted with ethyl acetate and the organic phase washed with water and brine, dried and concentrated in vacuo. The residue was purified by silica gel chromatography to give the title compound (4.2 g, 34%); MS(ES+) m/e 350 [M+H]⁺.

Step 2. 4-[4-(1-Methoxyimino-indan-5-yl)-4-oxo-3-pyridin-4-yl-butanoyl]-piperidine-1-carboxylic acid benzyl ester The title compound was prepared from the product of Step 1 and the product of Example 31 Step 1 using the method described in Example 31 Step 3; MS(ES+) m/e 540 [M+H]+.

Step 3. 5-(5-Piperidine-4-yl-3-pyridin-4-yl-furan-2-yl)-indan-1-one O-methyl-oxime A stirred solution of concentrated sulphuric acid (10 ml) was treated with the product of Step 2 (1.08 g, 2 mmol). After 30 minutes the reaction mixture was poured into ice-water containing 50% aqueous sodium hydroxide and the pH Step 4. 5-(5-Piperidin-4-yl-3-pyridin-4-yl-furan-2-yl)-indan-1-one The title compound was prepared from the product of Step 3 using the methods described in Example 1 Step 2; MS(ES+) m/e 359 [M+H]⁺.

Step 5. 5-(5-Piperidin-4-yl-3-pyridin-4-yl-furan-2-yl)-indan-1-one oxime

The title compound was prepared from the product of Step 4 using the methods described in Example 1 Step 3; MS(ES+) m/e 374 [M+H]+.

EXAMPLE 41

5-{5-[1-(2-Methoxyethyl)piperidin-4-yl]-3-pyridinyl-4-yl-furan-2-yl}indan-1-one oxime

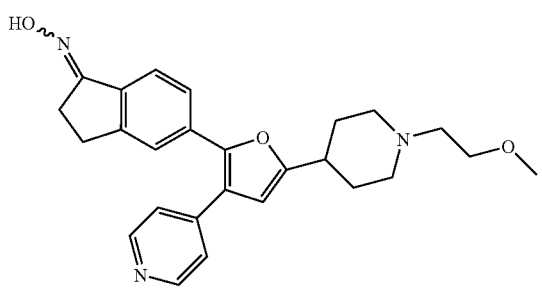

Step 1. 5-{5-[1-(2-Methoxyethyl)piperidin-4-yl-3-pyridin-4-ylfuran-2-yl}indan-1-one The title compound (0.086 g, 37%) was prepared from the product of Example 40 Step 4 and methoxyacetaldehyde (0.035 g, 0.56 mmol) (E. M. Acton et al, *J. Med. Chem.*, 1986, 29, 2074) using the method of Example 32; MS(ES+) m/e 417 [M+H]⁺.

Step 2. 5-{5-[1-(2-Methoxyethyl)piperidin-4-yl]-3-pyridin-4-ylfuran-2-yl}indan-1-one oxime The title compound (0.080 g, 98%) was prepared from the product of Step 1 using the method of Example 1 Step 3; MS(ES+) m/e 432 [M+H]⁺.

The following examples were prepared from the product of Example 40 Step 4 by the general two step method described in Example 41.

| Example | Aldehyde/Ketone | Characterisation |
| --- | --- | --- |
| 42 5-[5-(1-Cyclopropylmethylpiperidin-4-yl)-3-pyridin-4-ylfuran-2-yl]indan-1-one oxime | Cyclopropane carboxaldehyde | MS(ES+) m/e 428 [M + H]+ |
| 43 5-[5-(1-Cyclopentylpiperidin-4-yl)-3-pyridin-4-ylfuran-2-yl]indan-1-one oxime | Cyclopentanone | MS(ES+) m/e 442 [M + H]+ |
| 44 5-(5-{1-[2-(4-Chlorophenoxy)ethyl]-piperidin-4-yl}-3-pyridin-4-ylfuran-2-yl)indan-1-one oxime | (4-Chlorophenoxy) acetaldehyde (Maguire et al, J. Chem. Soc. 1954, 3669) | MS(ES+) m/e 528, 530 [M + H]+ |

EXAMPLE 45

{4-[5-(1-Hydroxyiminoindan-5-yl)-4-pyridin-4-ylfuran-2-yl]piperidin-1-yl}acetonitrile

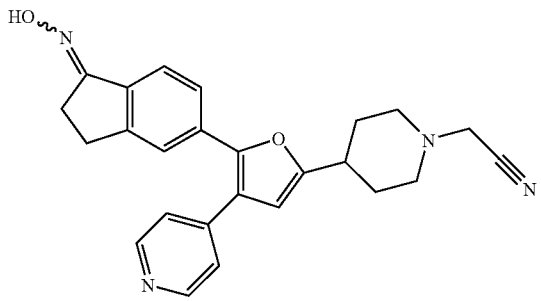

A solution of the product of Example 40 Step 5 (0.13 g, 0.35 mmol) in dry dichloromethane (10 ml) and dry dimethylformamide (0.5 ml) was treated with bromoacetonitrile (0.027 ml, 0.39 mmol) and triethylamine (0.054 ml, 0.39 mmol) and stirred at ambient temperature overnight. The crude reaction mixture was poured onto an SCX column and eluted with methanol followed by a mixture of 0.880 ammonia/methanol (1:10). The basic fractions were combined, concentrated in vacuo and triturated with diethyl ether to afford the title compound (0.13 g, 90%); MS(ES+) m/e 413 [M+H]+.

EXAMPLE 46

5-{5-[1-(2-Hydroxyethyl)piperidin-4-yl]-3-pyridin-4-ylfuran-2-yl}indan-1-one oxime

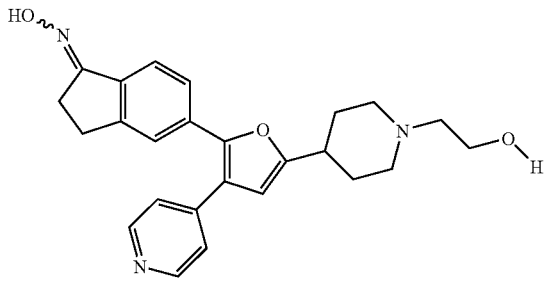

Step 1. 5-(5-{1-[2-(tert-Butyldimethylsilanyloxy)ethyl]piperidin-4-yl}-3-pyridin-4-ylfuran-2-yl)indan-1-one The title compound (0.14 g, 65%) was prepared from the product of Example 40 Step 4 and t-butyldimethylsilanyloxy acetaldehyde using the method of Example 32; MS(ES+) m/e 517 [M+H]+.

Step 2. 5-{5-[1-(2-Hydroxyethyl)piperidin-4-yl]-3-pyridin-4-ylfuran-2-yl)indan-1-one A solution of the product of Step 1 (0.135 g, 0.26 mmol) in dry tetrahydrofuran (5 ml) was cooled to 0° C. and treated dropwise with tetrabutylammonium fluoride (1.0M solution in tetrahydrofuran, 0.078 ml, 0.78 mmol) and allowed to warm to room temperature. After stirring for 2 hours, the reaction mixture was diluted with water, extracted with dichloromethane. The organic layer was then washed with saturated aqueous brine, dried (MgSO$_4$) and evaporated in vacuo. The residue was chromatographed on silica gel eluting with 0.880 ammonia/methanol/dichloromethane (0.5:4.5:95) to afford the title compound (0.027 g, 26%); MS(ES+) m/e 403 [M+H]+.

Step 3. 5-{5-[1-(2-Hydroxyethyl)piperidin-4-yl]-3-pyridin-4-ylfuran-2-yl}indan-1-one oxime The title compound (0.080 g, 77%) was prepared from the product of Step 2 using the method of Example 1 Step 3; MS(ES+) m/e 418 [M+H]+.

EXAMPLE 47

5-{5-[1-(2-Morpholin-4-ylethanoyl)piperidin-4-yl]-3-pyridin-4-ylfuran-2-yl}indan-1-one oxime

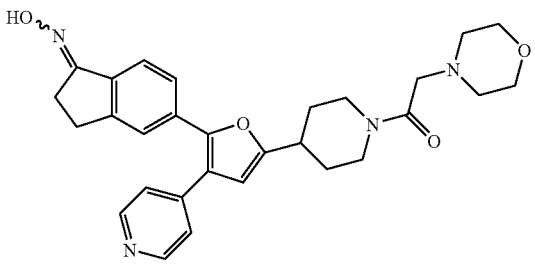

Step 1. 5-{5-[1-(2-Chloroethanoyl)piperidin-4-yl]-3-pyridin-4-ylfuran-2-yl}indan-1-one A solution of the product of Example 40 Step 4 (0.9 g, 2.5 mmol) in dry dichloromethane (10 ml) was cooled to 0° C., treated with triethylamine (0.38 ml, 2.7 mmol) and chloroacetyl chloride (0.22 ml, 2.7 mmol) and stirred at ambient temperature for 18 hours. The reaction mixture was poured into dichloromethane, washed with saturated aqueous sodium hydrogen carbonate solution and saturated sodium chloride solution, dried (MgSO$_4$) and evaporated in vacuo to afford the title compound (0.97 g, 89%); MS(ES+) m/e 435 [M+H]+.

Step 2. 5-{5-[1-(2-Morpholin-4-ylethanoyl)piperidin-4-yl]-3-pyridin-4-ylfuran-2-yl}indan-1-one A solution of the product of Step 1 (0.15 g, 0.35 mmol) in dry dichloromethane (3 ml) was treated with morpholine (0.060 ml, 0.76 mmol) and triethylamine (0.11 ml, 0.76 mmol) and stirred at ambient temperature for 18 hours. The reaction mixture was diluted with dichloromethane, washed with water and saturated sodium chloride solution, dried $MgSO_4$) and evaporated in vacuo. The residue was chromatographed on silica gel eluting with a mixture of 0.880 ammonia/methanol/dichloromethane (0.5:4.5:95) to afford the title compound (0.05 g, 29%); MS(ES+) m/e 486 [M+H]$^+$.

Step 3. 5-{5-[1-(2-Morpholin-4-ylethanoyl)piperidin-4-yl]-3-pyridin-4-ylfuran-2-yl}indan-1-one oxime The title compound (0.036 g, 72%) was prepared from the product of Step 2 using the method of Example 1 Step 3. 1H NMR (CDCl3) major isomer 10.96 (1H, s), 8.55 (2H, d, J 7 Hz) 7.52 (1H, d, J 8 Hz), 7.47 (1H, s), 7.37 (2H, d, J 7 Hz), 7.30 (1H, d, J 8 Hz), 6.57 (1H, s), 4.35 (1H, br d, J 13 Hz), 4.09 (1H, br d, J 13 Hz), 3.57 (5H, m), 3.47-2.63 (8H, m), 2.42 (4H, m), 2.03 (2H, m), 1.80-1.35 (2H, m)

EXAMPLE 48

5-{5-[1-(2-Piperidin-1-ylethanoyl)piperidin-4-yl]-3-pyridin-4-ylfuran-2-yl}indan-1-one oxime

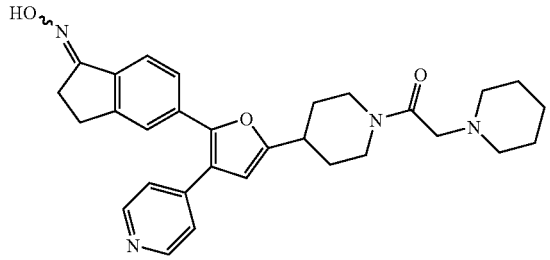

Step 1. 5-{5-[1-(2-Piperidin-5-ylethanoyl)piperidin-4-yl]-3-pyridin-4-ylfuran-2-yl}indan-1-one The title compound (0.03 g, 18%) was prepared from the product of Example 47 Step 1 and piperidine using the method of Example 47 Step 2; MS(ES+) m/e 484 [M+H]$^+$.

Step 2. 5-{5-[1-(2-Piperidin-1-ylethanoyl)piperidin-4-yl]-3-pyridin-4-ylfuran-2-yl}indan-1-one oxime The title compound (0.03 g, 100%) was prepared from the product of Step 1 using the method of Example 1 Step 3; MS(ES+) m/e 499 [M+H]$^+$.

EXAMPLE 49

5-{5-[1-(2-piperazin-1-ylethanoyl)piperidin-4-yl]-3-pyridin-4-ylfuran-2-yl}indan-1-one oxime

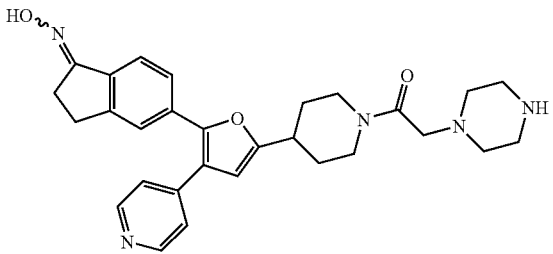

Step 1. 5-{5-[1-(2-piperazin-1-ylethanoyl)piperidin-4-yl]-3-pyridin-4-ylfuran-2-yl}indan-1-one The title compound (0.047 g, 17%) was prepared from the product of Example 47 Step 1 and piperazine using the method of Example 47 Step 2; MS(ES+) m/e 485 [M+H]$^+$.

Step 2. 5-{5-[1-(2-piperazin-1-ylethanoyl)piperidin-4-yl]-3-pyridin-4-ylfuran-2-yl}indan-1-one oxime The title compound (0.043 g, 86%) was prepared from the product of Step 1 using the method of Example 1 Step 3. MS(ES+) m/e 500 [M+H]$^+$.

EXAMPLE 50

5-(5-Piperidin-3-yl-2-pyridin-4-yl-furan-3-yl)-indan-1-one oxime

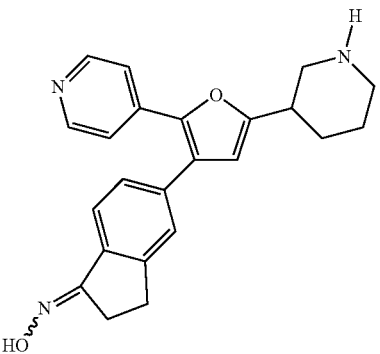

Step 1. 3-(Methoxy-methyl-carbamoyl)-piperidine-1-carboxylic acid benzyl ester A solution of piperidine-1,3-dicarboxylic acid 1-benzyl ester (G. Taylor et al, *Tetrahedron Lett.*, 1996, 37, 8, 1297) (15 g, 57 mmol) in dimethylformamide (57 ml) was treated with 1,1'-carbonyldiimidazole (15.7 g, 97 mmol). After stirring for 30 minutes, N,O-dimethylhydroxylamine hydrochloride (10.0 g, 102 mmol) was added and the mixture stirred for a further 1 hour. The reaction mixture was poured into 2M hydrochloric acid and extracted with ethyl acetate. The organic layer was washed successively with water, saturated aqueous sodium hydrogen carbonate solution, water and brine, dried and concentrated in vacuo to give the title compound (16.9 g, 97%); MS(ES+) m/e 307 [M+H]$^+$.

Step 2. 3-Acetyl-piperidine-1-carboxylic acid benzyl ester

A cooled solution of the product of Step 1 (16.85 g, 55 mmol) in tetrahydrofuran (300 ml) at −10° C. was treated with methylmagnesium bromide (37 ml, 3M solution in diethyl ether, 111 mmol). The reaction was allowed to warm to room temperature and stirred for a further 30 minutes. The mixture was then poured into 2M hydrochloric acid and the product extracted into ethyl acetate. The organic layer was washed with water and brine, dried and concentrated to yield the title compound (13.4 g, 93%); MS(ES+) m/e 284 [M+Na]$^+$.

Step 3. 3-[(E)-3-(1-Methoxyimino-indan-5-yl)-allanoyl]-piperidine-1-carboxylic acid benzyl ester The title compound (6.20 g, 43%) was prepared from the product of Step 2 (8.65 g, 33.1 mmol) using the method of Example 31 step 2; MS(ES−) m/e 431 [M−H]$^−$.

Step 4. 3-[3-(3-Methoxyimino-indan-5-yl)-4-oxo-4-pyridin-4-ylbutanoyl]-piperidine-1-carboxylic acid benzyl ester The title compound (5.2 g, 67%) was prepared from the product of step 3 by the method of example 31, step 3; MS(ES+) m/e 540 [M+H]+.

Step 5. 3-[4-(1-Oxo-indan-5-yl)-5-pyridin-4-yl-furan-2-yl]-piperidine-1-carboxylic acid benzyl ester A solution of the product of Step 4 (4.0 g, 7.42 mmol) in 1,4-dioxane (100 ml) and acetone (250 ml) was treated with 5M hydrochloric acid (50 ml) and the mixture heated at 90° C. for 5 hours. After cooling to room temperature, the reaction was concentrated and re-dissolved in chloroform and saturated aqueous sodium hydrogen carbonate solution. The organic phase was dried, concentrated in vacuo and purified by silica gel chromatography eluting with ethyl acetate/dichloromethane (4:6) to yield the title compound (2.50 g, 69%); MS(ES+) m/e 493 [M+H]+.

Step 6. 5-(5-Piperidin-3-yl-2-pyridin-4-yl-furan-3-yl)-indan-1-one

A solution of the product of Step 5 (2.3 g, 4.67 mmol) in ethanol (100 ml) and cyclohexene (60 ml) was treated with 10% palladium on charcoal (0.8 g) and heated at 90° C. for 1.5 hours. After cooling to room temperature, the reaction mixture was filtered through celite and washed several times with ethanol. The filtrate was evaporated in vacuo and the residue purified by silica gel chromatography eluting with chloroform/ethanol/0.880 ammonia solution (95:4.5:0.5) followed by (90:9:1) to yield the title compound (1.47 g, 88%); MS(ES+) m/e 359 [M+H]+.

Step 7. 5-(5-Piperidin-3-yl-2-pyridin-4-yl-furan-3-yl)-indan-1-one oxime

The title compound was prepared from the product of Step 6 using the method described in Example 1 Step 3; MS(ES+) m/e 374 [M+H]+.

EXAMPLE 51

5-[5-(1-Methyl-piperidin-3-yl)-2-pyridin-4-yl-furan-3-yl]-indan-1-one oxime

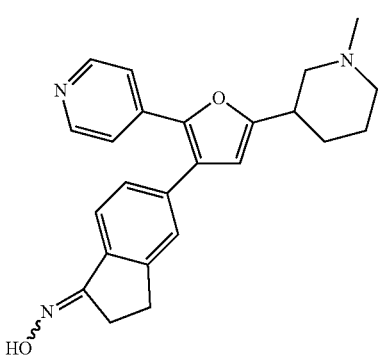

Step 1. 5-[5-(1-Methyl-piperidin-3-yl)-2-pyridin-4-yl-furan-3-yl]-indan-1-one

A solution of the product of Example 50 Step 6 (100 mg, 0.28 mmol) in acetone (10 ml) was treated with potassium carbonate (116 mg, 0.84 mmol) followed by methyl iodide (0.019 ml, 0.31 mmol) at 0° C. The reaction was allowed to warm to room temperature and stirred for a further 18 hours. The mixture was diluted with chloroform, washed with saturated aqueous sodium hydrogen carbonate solution, dried and concentrated in vacuo. The residue was purified by silica gel chromatography eluting with chloroform/ethanol/0.880 ammonia solution (98:1.8:0.2) to yield the tide compound (40 mg, 38%); MS(ES+) m/e 373 [M+H]+.

Step 2. 5-[5-(1-Methyl-piperidin-3-yl)-2-pyridin-4-yl-furan-3-yl]-indan-1-one oxime The title compound was prepared from the product of Step 1 using the method described in Example 1 Step 3. MS(ES+) m/e 388 [M+H]+.

EXAMPLE 52

N-Hydroxy-2-{3-[4-(1-hydroxyimino-indan-5-yl)-5-pyridin-4-yl-furan-2-yl]-piperidin-1-yl}-acetamidine

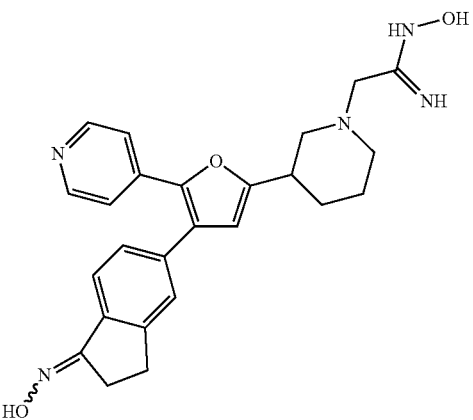

Step 1. {3-[4-(1-Oxo-indan-5-yl)-5-pyridin-4-yl-furan-2-yl]-piperidin-1-yl}-acetonitrile A solution of the product of Example 50 Step 6 (150 mg, 0.41 mmol) in dichloromethane (10 ml) was treated with triethylamine (0.064 ml, 0.46 mmol) and bromoacetonitrile (55 mg, 0.45 mmol). The reaction was stirred at room temperature for 18 hours and then diluted with chloroform, washed with saturated aqueous sodium hydrogen carbonate solution, dried and concentrated in vacuo. The residue was purified by silica gel chromatography eluting with chloroform/ethanol/0.880 ammonia solution (98:1.8:0.2) to yield the title compound (126 mg, 76%); MS(ES+) m/e 398 [M+H]+.

Step 2. N-Hydroxy-2-{3-[4-(1-hydroxyimino-indan-5-yl)-5-pyridin-4-yl-furan-2-yl]-piperidin-1-yl}-acetamidine The title compound was prepared from the product of Step 1 using the method described in Example 1 Step 3. MS(ES+) m/e 446 [M+H]+.

EXAMPLE 53

5-{5-[1-(2-Methoxy-ethyl)-piperidin-3-yl]-2-pyridin-4-yl-furan-3-yl}-indan-1-one oxime

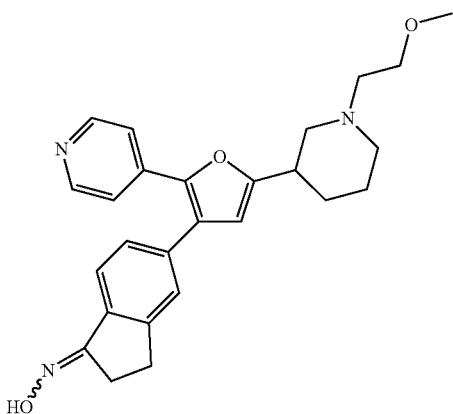

Step 1. 5-{5-[1-(2-Methoxy-ethyl)-piperidin-3-yl]-2-pyridin-5-yl-furan-3-yl}-indan-5-one The title compound was prepared from the product of Example 50 Step 6 and methoxyacetaldehyde {E. M. Acton et al, *J. Med. Chem.*, 1986, 29, 2074} using the method described in Example 32. MS(ES+) m/e 417 [M+H]+.

Step 2. 5-{5-[1-(2-Methoxy-ethyl)-piperidin-3-yl]-2-pyridin-4-yl-furan-3-yl}-indan-1-one oxime The title compound was prepared from the product of Step 1 using the method described in Example 1 Step 3. MS(ES+) m/e 432 [M+H]+.

EXAMPLE 54

5-[5-(1-Cyclopropylmethyl-piperidin-3-yl)-2-pyridin-4-yl-furan-3-yl]-indan-1-one oxime

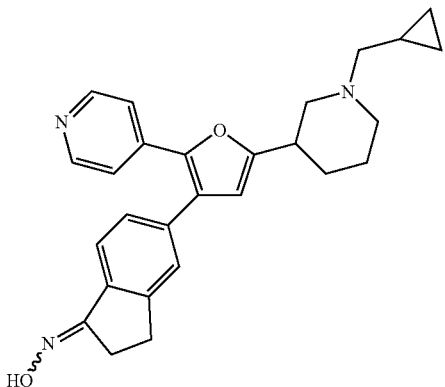

Step 1. 5-[5-(1-Cyclopropylmethyl-piperidin-3-yl)-2-pyridin-4-yl-furan-3-yl]-indan-1-one The title compound was prepared from the product of Example 50 Step 6 and cyclopropanecarboxaldehyde using the method described in Example 32; MS(ES+) m/e 413 [M+H]+.

Step 2. 5-[5-(1-Cyclopropylmethyl-piperidin-3-yl)-2-pyridin-4-yl-furan-3-yl]-indan-1-one oxime The title compound was prepared from the product of Step 1 using the method described in Example 1 Step 3; MS(ES+) m/e 428 [M+H]+.

EXAMPLE 55

5-{5-[1-(2-Morpholin-4-yl-ethanoyl)-piperidin-3-yl]-2-pyridin-4-yl-furan-3-yl}-indan-1-one oxime

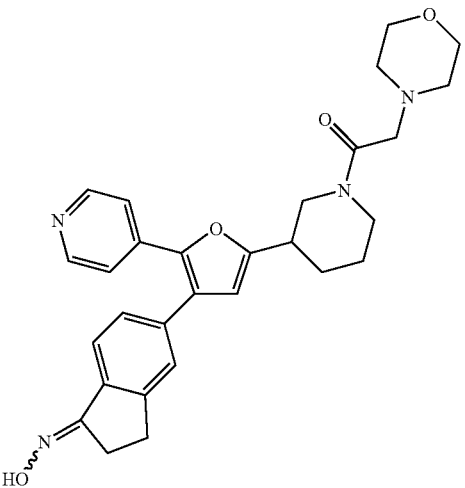

Step 1. 5-{5-[1-(2-Chloro-ethanoyl)-piperidin-3-yl]-2-pyridin-4-yl-furan-3-yl}-indan-1-one A solution of the product from Example 50 Step 6 (800 mg, 2.23 mmol) in dry dichloromethane was cooled to 0° C. and treated with triethylamine (0.33 ml, 2.37 mmol) and chloroacetyl chloride (0.19 ml, 2.38 mmol). The reaction was allowed to warm to room temperature and then poured into dichloromethane, washed with saturated aqueous sodium hydrogen carbonate solution and brine, dried and concentrated in vacuo. The residue was purified by silica gel chromatography eluting with chloroform/ethanol/0.880 ammonia solution (98:1.8:0.2) to yield the title compound (700 mg, 72%); MS(ES+) m/e 435/437 [M+H]+.

Step 2. 5-{5-[1-(2-Morpholin-4-yl-ethanoyl)-piperidin-3-yl]-2-pyridin-4-yl-furan-3-yl}-indan-1-one A solution of the product of Step 1 (140 mg, 0.32 mmol) in dry dichloromethane (10 ml) was treated with morpholine (0.031 ml, 0.35 mmol) and triethylamine (0.049 ml, 0.35 mmol) and heated at reflux for 3 hours. The reaction mixture was diluted with dichloromethane and washed with saturated aqueous sodium hydrogen carbonate solution. The organic phase was dried, concentrated in vacuo and then purified by silica gel chromatography eluting with chloroform/ethanol/ 0.880 ammonia solution (98:1.8:0.2) to yield the title compound (85 mg, 55%); MS(ES+) m/e 486 [M+H]+.

Step 3. 5-{5-[1-(2-Morpholin-4-yl-ethanoyl)-piperidin-3-yl]-2-pyridin-4-yl-furan-3-yl}-indan-1-one oxime The title compound was prepared from the product of Step 2 using the method described in Example 1 Step 3. MS(ES+) m/e 501 [M+H]+.

The following examples were prepared from the product of Example 55 Step 1 using the general two-step method described in Example 55 Steps 2 and 3.

| Example | Amine | Characterisation |
|---|---|---|
| 56 5-{5-[1-(2-Piperidin-1-yl-ethanoyl)-piperidin-3-yl]-2-pyridin-4-yl-furan-3-yl}-indan-1-one oxime | Piperidine | MS(ES+) m/e 499 [M + H]⁺ |
| 57 5-{2-Pyridin-4-yl-5-[1-(2-pyrrolidin-1-yl-ethanoyl)-piperidin-3-yl]-furan-3-yl}-indan-1-one oxime | Pyrrolidine | MS(ES+) m/e 485 [M + H]⁺ |
| 58 5-(5-{1-[2-(4-Methyl-piperazin-1-yl)-ethanoyl]-piperidin-3-yl}-2-pyridin-4-yl-furan-3-yl)-indan-1-one oxime | 1-Methyl-piperazine | MS(ES+) m/e 514 [M + H]⁺ |
| 59 5-[5-(1-{2-[4-(2-Methoxy-ethyl)-piperazin-1-yl]-ethanoyl}-piperidin-3-yl)-2-pyridin-4-yl-furan-3-yl]-indan-1-one oxime | 1-(2-Methoxy-ethyl)-piperazine | MS(ES+) m/e 558 [M + H]⁺ |

The following examples were prepared from the product of Example 29 using the general method described in Example 32.

| Example | Amine | Characterisation |
|---|---|---|
| 60 5-{5-[4-Hydroxy-1-(2-methoxyethyl)-piperidin-4-yl]-2-pyridin-4-yl-furan-3-yl}-indan-1-one oxime | Methoxyacetaldehyde | MS(ES+) m/e 448 [M + H]⁺ |
| 61 5-[5-(1-Cyclopropylmethyl-4-hydroxy-piperidin-4-yl)-2-pyridin-4-yl-furan-3-yl]-indan-1-one oxime | Cyclopropanecarbaldehye | MS(ES+) m/e 444 [M + H]⁺ |

EXAMPLE 62

5-(5-Hydroxymethyl-2-pyridin-4-yl-furan-3-yl)indan-1-one oxime

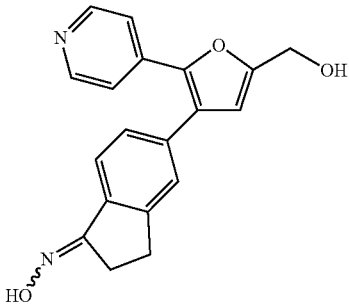

Step 1. (4,5-Dibromofuran-2-yl)-methanol

A solution of 4,5-dibromofuroic acid (13.49 g, 50 mmol) and N-methyl morpholine (6.05 ml, 55 mmol in tetrahydrofuran (200 ml) at 0° C. as treated with isobutyl chloroformate (6.81 ml, 53 mmol). After stirring at 0° C. for 45 minutes sodium borohydride (11.35 g, 300 mmol) was added portionwise followed by saturated sodium bicarbonate solution (2 ml) and the mixture allowed to reach room temperature over 16 hours. The solution was evaporated in vacuo and the solid residue slurried in ethyl acetate. The solids were filtered and washed with ethyl acetate. The combined filtrates were dried over anhydrous sodium sulfate and concentrated in vacuo. The residue was purified by silica gel chromatography eluting with dichloromethane to afford the title product as a colourless solid, (10 g, 78%); ¹H NMR (CDCl₃) 6.38 (1H, s), 4.56 (2H, d, J 6.4 Hz), 1.80 (1H, t, J 6.4 Hz).

Step 2. (4-Bromo-5-pyridin-4-yl-furan-2-yl)-methanol

The product from Step 1 (2.55 g, 10 mol), 4-pyridyltributyl stannane (3.86 g, 10 mmol) and bis(triphenylphosphine) palladium (II) chloride (351 mg, 0.5 mmol) in toluene (50 ml) was heated at reflux for 18 hours. After cooling the solution was concentrated in vacuo and the residue purified by silica gel chromatography, eluting with 5% methanol in dichloromethane to afford the title product (737 mg) which was used directly in Step 3; MS(ES+) m/e 254, 256

Step 3. 5-(5-Hydroxymethyl-2-pyridin-4-yl-furan-3-yl)indan-1-one

The product from Step 2 (737 mg, 2.9 mmol), 5-(4,4,5,5-tetramethyl-[1,3,2]-dioxaborolan-2-yl)indanone (0.25 g, 1 mmol) (WO98/45265) (750 mg, 2.9 mmol), potassium acetate (854 mg, 8.7 mmol), triphenylphosphine (79 mg, 0.3 mmol) and palladium (II) acetate (34 mg, 0.15 mmol) were heated at 95° C. in 1:1:1 ethanol:water:N,N-dimethylformamide (10 ml) for 16 hours. After cooling the solution was partitioned between ethylacetate/water and the aqueous phase extracted with ethylacetate (×3). The combined organic extracts were washed with water (×3), brine, dried over anhydrous magnesium sulfate and concentrated in vacuo. The residue was purified by silica gel chromatography eluting with ethylacetate to afford the title product (383 mg, 43%); MS(ES+) m/e 306 [M+H]⁺.

Step 4. 5-(5-Hydroxymethyl-2-pyridin-4-yl-furan-3-yl)indan-1-one oxime

The product of Step 3 (150 mg, (0.49 mmol) was heated at reflux in ethanol (10 ml) containing 50% aqueous hydroxylamine (1 ml) for 2 hours. The solution was concentrated in vacuo to an oil and purified by silica gel chromatography eluting with 1:9:90.880 ammonia:ethanol:dichloromethane to afford the title product (128 mg, 81%); MS(ES+) m/e 321 [M+H]⁺.

It is to be understood that the present invention covers all combinations of particular and preferred subgroups described hereinabove.

BIOLOGICAL EXAMPLES

The activity of compounds of formula (I) as B-Raf inhibitors may be determined by the following in vitro assay:

Fluorescence Anisotropy Kinase Binding Assay

The kinase enzyme, fluorescent ligand and a variable concentration of test compound are incubated together to reach thermodynamic equilibrium under conditions such that in the absence of test compound the fluorescent ligand is significantly (>50%) enzyme bound and in the presence of a sufficient concentration (>10×Ki) of a potent inhibitor the anisotropy of the unbound fluorescent ligand is measurably different from the bound value.

The concentration of kinase enzyme should preferably be ≧1×$K_f$. The concentration of fluorescent ligand required will depend on the instrumentation used, and the fluorescent and physicochemical properties. The concentration used must be lower than the concentration of linase enzyme, and preferably less than half the kinase enzyme concentration. A typical protocol is:

All compounds are serially diluted in DMSO, then by a one step dilution into buffer of comparison, 50 mM HEPES, pharmaceutical pH7.5, 1 mM CHAPS, 10 mM $MgCL_2$, for the assay.

B-Raf Enzyme concentration: 1 nM
Fluorescent ligand concentration: 0.5 nM
Test compound concentration: 0.5 nM-100 uM
Components incubated in 10 ul final volume in LJL HE 384 type B black microtitre plate until equilibrium reached (Over 3 h, up to 30 h)
Fluorescence anisotropy read in an LJL Acquest fluorescence reader.

Definitions: Ki=dissociation constant for inhibitor binding
Kf=dissociation constant for fluorescent ligand binding
The fluorescent ligand is the following compound:

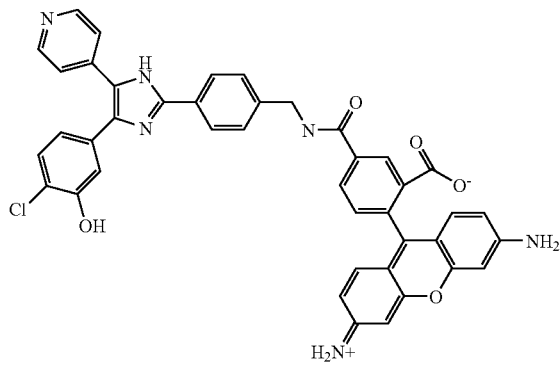

which is derived from 5-[2-(4-aminomethylphenyl)-5-pyridin4-yl-1H-imidazol-4-yl]-2-chlorophenol and rhodamine green.

Compounds of the invention have a $K_d$ of less than 1 μM.

Raf Kinase Assay (Assay 1)

Activity of human recombinant B-Raf protein was assessed in vitro by assay of the incorporation of radiolabelled phosphate to recombinant MAP kinase kinase (MEK), a known physiologic substrate of B-Raf. Catalytically active human recombinant B-Raf protein was obtained by purification from Sf9 insect cells infected with a human B-Raf recombinant baculovirus expression vector. To ensure that all substrate phosphorylation resulted from B-Raf activity, a catalytically inactive form of MEK was utilised. This protein was purified from bacterial cells expressing mutant inactive MEK as a fusion protein with glutathione-S-transferase (GST-kdMEK).

Method: Standard assay conditions of B-Raf catalytic activity utilised 3 ug of GST-kdMEK, 10 uM ATP and 2uCi $^{33}$P-ATP, 50 mM MOPS, 0.1 mM EDTA, 0.1M sucrose, 10 mM $MgCl_2$ plus 0.1% dimethylsulphoxide (containing compound where appropriate) in a total reaction volume of 30 ul. Reactions were incubated at 25° C. for 90 minutes and reactions terminated by addition of ethylenediaminetetraacetic acid (EDTA) to a final concentration of 50 uM. 10 ul of reaction was spotted to P81 phosphocellulose paper and air dried. Following four washes in ice cold 10% trichloroacetic acid, 0.5% phosphoric acid, papers were air dried prior to addition of liquid scintillant and measurement of radioactvity in a scintillation counter.

Results: The compounds of the examples were found to be effective in inhibiting B-Raf mediated phosphorylation of GST-kdMEK substrate having $IC_{50}$'s of <3 μM.

The activity of compounds as Raf inhibitors may also be determined by the assays described in WO 99/10325; McDonald, O. B., Chen, W. J., Ellis, B., Hoffman, C., Overton, L., Rink, M., Smith, A., Marshall, C. J. and Wood, E. R. (1999) A scintillation proximity assay for the Raf/MEK/ERK kinase cascade: high throughput screening and identification of selective enzyme inhibitors, Anal. Biochem. 268: 318-329 and AACR meeting New Orleans 1998 Poster 3793.

The neuroprotective properties of B-Raf inhibitors may be determined by the following in vitro assay:

Neuroprotective Properties of B-Raf Inhibitors in Rat Hippocampal Slice Cultures Organotypic cultures provide an intermediate between dissociated neuronal cell cultures and in-vivo models of oxygen and glucose deprivation (OGD). The majority of glial-neuronal interactions and neuronal circuitry are maintained in cultured hippocampal slices, so facilitating investigation of the patterns of death among differing cell types in a model that resembles the in vivo situation. These cultures allow the study of delayed cellular damage and death 24 hours, or more, post-insult and permit assessment of the consequences of long-term alterations in culture conditions. A number of laboratories have reported delayed neuronal damage in response to OGD in organotypic cultures of the hippocampus (Vornov et al., Stroke, 1994, 25, 57-465; Newell et al., Brain Res., 1995, 676, 38-44). Several classes of compounds have been shown to protect in this model, including EAA antagonists (Strasser et al., Brain Res., 1995, 687, 167-174), Na channel blockers (Tasker et al., J. Neurosci., 1992, 12, 98-4308) and Ca channel blockers (Pringle et al., Stroke, 1996, 7, 2124-2130). To date, relatively little is known of the roles of intracellular kinase mediated signalling pathways in neuronal cell death in this model.

Method:

Organotypic hippocampal slice cultures were prepared using the method of Stoppini et al., J. Neurosci. Methods, 1995, 37, 173-182. Briefly, 400 micron sections prepared from hippocampi of 7-8 day postnatal Sprague Dawley rats are cultured on semiporous membranes for 9-12 days. OGD is then induced by incubation in serum and glucose-free medium in an anaerobic chamber for 45 minutes. Cultures are then returned to the air/$CO_2$ incubator for 23 hours before analysis. Propidium iodide (PI) is used as an indicator of cell death. PI is non toxic to neurones and has been used in many studies to ascertain cell viability. In damaged neurons PI enters and binds to nucleic acids. Bound PI shows increased emission at 635 nm when excited at 540 nm. One PI fluorescence image and one white light image are taken and the proportion of cell death analysed. The area of region CA1 is defined from the white light image and superimposed over the PI image. The PI signal is thresholded and area of PI damage expressed as a percentage of the CA1 area. Correlation between PI fluorescence and histologically confirmed cell death has been validated previously by Nissl-staining using cresyl fast violet (Newell et al., *J. Neurosci.*, 1995, 15, 7702-7711).

The anti-cancer properties of compounds of the invention may be determined by the following in vitro assays:

Methylene Blue Growth Inhibition Assay (Assay 2)

Normal human foreskin fibroblasts (HFF), human melanoma (A375P, SKMEL2, SKMEL3) colon carcinoma (Colo 205) were cultured in the following growth media: A375P, Colo 205, Roswell Park Memorial Institute (RPMI) 1640 (Life Technologies 22400-089) containing 10% fetal bovine serum (FBS); HFF, Dulbecco's modified Eagle Medium (DMEM) (Life Technologies 12320-032) containing 10% FBS; SKMEL2 and SKMEL3, Minimum Essential Medium (MEM, Life Technologies 11095-080) containing 1× non-essential amino acids (Life Technologies 11140-050) and 10% FBS. Cells were harvested using 0.25% trypsin/1 mM, EDTA, counted using a haemocytometer, and plated in 100 microliters of the appropriate media, at the following densities, in a 96-well tissue culture plate Falcon 3075): HFF and A375P, 5,000 cells/well; all other cell lines, 10,000 cells/well. The next day, compounds were diluted in RPMI containing 100 micrograms/ml gentamicin, at twice the final required concentration, from 10 mM stock solutions in dimethyl sulphoxide (DMSO). One hundred microliters per well of these dilutions were added to the 100 microliters of media currently on the cell plates. RPMI containing 0.6% DMSO was added to control wells. Compounds diluted in. The final concentration of DMSO in all wells was 0.3%. Cells were incubated at 37° C., 5% $CO_2$ for 3 days. Medium was removed by aspiration. Cell biomass was estimated by staining cells with 90 μl per well methylene blue (Sigma M9140, 0.5% in 50:50 ethanol:water) and incubation at room temperature for at least 30 minutes. Stain was removed, the plates rinsed by immersion in deionized water and air-dried. To release stain from the cells 100 μl of solubilization solution was added (1% N-lauroyl sarcosine, sodium salt, Sigma L5125, in phosphate-buffered saline solution (PBS)), and plates were incubated at room temperature for 30 minutes. Optical density at 620 nM was measured on a microplate reader. Percent inhibition of cell growth was calculated relative to vehicle treated control wells. Concentration of compound that inhibits 50% of cell growth ($IC_{50}$) was interpolated using nonlinear regression (Levenberg-Marquardt) and the equation, $y=V_{max}*(1-(x/(K+x)))+Y2$, where "K" was equal to the $IC_{50}$.

XTT 72 hr Growth Inhibition Protocol for Mammalian Cultured Cells (Assay 3)

Human diploid foreskin fibroblasts (HFF) or human colon carcinoma (Colo 201) cells were grown in Dulbecco's modified Eagle's medium (DMEM) (Invitrogen/Life Technologies) containing 10% fetal bovine serum (FBS) and the antibiotics penicillin (100 Units/ml) and streotomycin (100 micrograms/ml) (Invitrogen/Life Technologies). Growth was at 37° C. in humidified 5% CO2 incubators in 75 $cm^2$ plastic flasks. Cells were harvested using 0.25% trypsin/1 mM ethylenediaminetetraacetic acid (EDTA), resuspended in growth medium, and counted using a hemocytometer. Flat-bottomed 96-well plates were seeded with $2 \times 10^3$ cells/well in a volume of 200 ul from trypsinized exponentially growing cultures. To "blank" wells, growth medium was added with no additions. Cells were incubated overnight to permit attachment.

Next day, medium from wells that contained cells was replaced with 180 microliters of fresh medium. Appropriate dilutions of test compounds were added to the wells from stock soloutions of compound dissolved in dimethyl sulfoxide DMSO); final DMSO concentration in all wells was 0.2%. Cells plus compound were incubated for an additional 72 hr at 37° C. under normal growth conditions. Cells were then assayed for viability using standard XTT/PMS*. Fifty microliters of XTT/PMS solution was added to each well and plates were incubated for 90 minutes at 37° C. Absorbance at 450 nM was then determined using a 96-well UV plate reader (Molecular Devices). Under these conditions, absorbance of untreated control cells at 450 nm was at least 1.0 optical density unit/ml. Percent viability of cells in each well was calculated from these data (having been corrected for background absorbance). It was equal to 100×(A450 test well/A450 untreated control well), the A450s being averages of triplicate determinations. IC50 was that concentration of compound that reduced cell viability to 50% of control (untreated) viability, as determined from plots of concentration vs percent viability.

*Preparation of XTT/PMS solution (immediately before assay).

For each 96-well plate, 8 mg XTT (2,3-bis[2-Methoxy4-nitro-5-sulfophenyl]-2H-tetrazolium-5-carboxanilide) (Sigma Chemical Co.) per plate was dissolved in 100 ul DMSO. 3.9 ml $H_2O$ was added to dissolve XTT and 20 ul of PMS (phenazine methosulfate, Sigma Chemical Co.) stock solution (30 mg/ml) was added from frozen aliquoted stock solution (10 mg of PMS in 3.3 ml phosphate buffered saline (Invitrogen/Life Technologies). (These stocks are routinely frozen at −20° C. until use).

Normal human foreskin fibroblasts (HFF) are the control normal cell line that should not be inhibited or at least much less sensitive.

| | | Cell Line Pathology | HFF normal | Colo201 Colorectal cancer | Colo205 Colorectal cancer | A375P melanoma | SKMEL3 melanoma | SKMEL2 melanoma |
|---|---|---|---|---|---|---|---|---|
| | | B-Raf Status | wt | ND | V599E | V599E | V599E | wt |
| | B-Raf, nM Kd | Ras Status | wt | ND | wt | wt | wt | [Q61R]N-Ras |
| Example No | Assay 1 | | | Assay 3 | Assay 3 | Assay 2 | Assay 2 | Assay 2 | Assay 2 |
| 1 | 7.2 | | | >30* | 0.49▵ | 0.75▵ | 1.3▵ | 5.3* | 4.2* |
| 5 | 3.6 | | | >30* | 0.89▵ | 0.23† | 0.60▵ | 5.4* | 2.5▵ |
| 31 | 2.4 | | | 21* | 0.01† | 0.010† | 0.043† | 0.65▵ | 0.17† |

*indicates IC50 > 3 μM
▵indicates IC 50 0.3-3 μM
†indicates IC50 < 0.3 μM
A375, Colo205 and SKMEL are reported as wild type (wt) for Ras status in the literature.
V599E indicates that the cell lines have activating BRaf mutation (V599E)
ND represents not determined Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

The application of which this description and claims forms part may be used as a basis for priority in respect of any subsequent application. The claims of such subsequent application may be directed to any feature or combination of features described herein. They may take the form of composition, process, or use claims and may include by way of example and without limitation the following claims.

The invention claimed is:

1. A compound of formula (I):

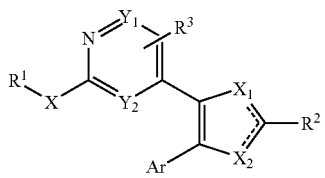

wherein:
X is O, $CH_2$, CO, S or NH, or the moiety X—$R^1$ is hydrogen;
$Y_1$ and $Y_2$ independently represent CH or N;
$R^1$ is hydrogen, $C_{1-6}$alkyl, $C_{3-7}$cycloalkyl, aryl, aryl-$C_{1-6}$alkyl-, heterocyclyl, heterocyclyl$C_{1-6}$alkyl-, heteroaryl, or heteroaryl$C_{1-6}$alkyl-, any of which, except hydrogen, may be optionally substituted;
$R^2$ is $C_{1-6}$alkyl, $C_{3-7}$cycloalkyl, heterocyclyl, heterocyclyl$C_{1-6}$alkyl-, $C_{1-6}$alkyloxy, $C_{1-6}$alkylthio, $C_{1-6}$alkylamino, or $C_{1-6}$alkylhetero$C_{1-6}$alkyl- any of which may be optionally substituted;
Ar is a group of the formula a) or b):

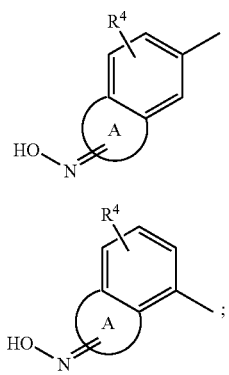

$R^3$ and $R^4$ are independently selected from hydrogen, halogen, $C_{1-6}$alkyl, aryl, aryl$C_{1-6}$alkyl, $C_{1-6}$alkoxy, $C_{1-6}$alkoxy$C_{1-6}$alkyl, halo$C_{1-6}$alkyl, aryl$C_{1-6}$alkoxy, hydroxy, nitro, cyano, azido, amino, mono- and di-N—$C_{1-6}$alkylamino, acylamino, arylcarbonylamino, acyloxy, carboxy, carboxy salts, carboxy esters, carbamoyl, mono- and di-N—$C_{1-6}$alkylcarbamoyl, $C_{1-6}$alkoxycarbonyl, aryloxycarbonyl, ureido, guanidino, $C_{1-6}$alkylguanidino, amidino, $C_{1-6}$alkylamidino, sulphonylamino, aminosulphonyl, $C_{1-6}$alkylthio, $C_{1-6}$alkyl sulphinyl or $C_{1-6}$alkylsulphonyl; and
one of $X_1$ and $X_2$ is selected from O, S or $NR^{11}$ and the other is CH, wherein $R^{11}$ is hydrogen, $C_{1-6}$alkyl, aryl or aryl$C_{1-6}$alkyl;
or a pharmaceutically acceptable salt thereof.

2. The compound according to claim 1 wherein X is NH or X—$R^1$ is hydrogen and when NH, $R^1$ is hydrogen or $C_{1-6}$-alkyl.

3. The compound according to claim 1, wherein $R^2$ is an optionally substituted heterocyclyl, heterocyclyl($C_{1-6}$)alkyl- or $C_{1-6}$alkylhetero$C_{1-6}$alkyl.

4. A compound, wherein the compound is selected from:
5-(5-Morpholin-4-ylmethyl-2-pyridin-4-yl-furan-3-yl)-indan-1-one oxime;
5-(5-Piperidin-1-ylmethyl-2-pyridin-4-yl-furan-3-yl)-indan-1-one oxime;
5-(2-Pyridin-4-yl-5-pyrrolidin-1-ylmethyl-furan-3-yl)-indan-1-one oxime;
5-{5-(4-Methyl-piperazin-1-ylmethyl)-2-pyridin-4-yl-furan-3-yl]-indan-1-one oxime;
5-[5-(1,1-Dioxo-1-thiomorpholin-4-ylmethyl)-2-pyridin-4-yl-furan-3-yl]-indan-1-one oxime;
5-(5-Piperazin-1-ylmethyl-2-pyridin-4-yl-furan-3-yl)-indan-1-one oxime;
5-(5-Dimethylaminomethyl-2-pyridin-4-yl-furan-3-yl)-indan-1-one oxime;
5-{5-[(2-Methoxyethylamino)-methyl]-2-pyridin-4-yl-furan-3-yl}-indan-1-one oxime;
5-(5-{[1-(2-Methoxy-ethyl)-piperidin-4-ylamino]-methyl}-3-pyridin-4-yl-furan-2-yl)-indan-1-one oxime;
5-(5-Morpholin-4-ylmethyl-3-pyridin-4-yl-furan-2-yl)-indan-1-one oxime;
5-(5-Piperidin-1-ylmethyl-3-pyridin-4-yl-furan-2-yl)-indan-1-one oxime;
5-[3-Pyridin-4-yl-5-(4-pyrrolidin-1-yl-piperidin-1-ylmethyl)-furan-2-yl]-indan-1-one oxime;
5-{5-[(2-Methoxy-ethylamino)-methyl]-3-pyridin-4-yl-furan-2-yl}-indan-1-one oxime;
5-(5-Diethylaminomethyl-3-pyridin-4-yl-furan-2-yl)-indan-1-one oxime;
5-[5-(4-Ethyl-piperazin-1-ylmethyl)-3-pyridin-4-yl-furan-2-yl]-indan-1-one oxime;
5-{5-[4-(2-Methoxy-ethyl)-piperazin-1-ylmethyl]-3-pyridin-4-yl-furan-2-yl}-indan-1-one oxime;
5-{5-[(2-Morpholin-4-yl-ethylamino)-methyl]-3-pyridin-4-yl-furan-2-yl}-indan-1-one oxime;
5-(5-{[Methyl-(1-methyl-piperidin-4-yl)-amino]-methyl}-3-pyridin-4-yl-furan-2-yl)-indan-1-one oxime;
5-[5-(4-Methyl-piperazin-1-ylmethyl)-3-pyridin-4-yl-furan-2-yl]-indan-1-one oxime;
5-(3-Pyridin-4-yl-5-pyrrolidin-1-ylmethyl-furan-2-yl)-indan-1-one oxime;
5-(5-Dimethylaminomethyl-3-pyridin-4-yl-furan-2-yl)-indan-1-one oxime;
5-{5-[4-(2-Hydroxy-ethyl)-piperazin-1-ylmethyl]-3-pyridin-4-yl-furan-2-yl}-indan-1-one oxime;
5-(5-{[(2-Methoxy-ethyl)-methyl-amino]-methyl}-3-pyridin-4-yl-furan-2-yl)-indan-1-one oxime;
5-(5-{[Isopropyl-(2-methoxy-ethyl)-amino]-methyl}-3-pyridin-4-yl-furan-2-yl)-indan-1-one oxime;
5-[5-(1,1-Dioxo-1-thiomorpholin-4-ylmethyl)-3-pyridin-4-yl-furan-2-yl]-indan-1-one oxime;
5-(5-Piperazin-1-ylmethyl-3-pyridin-4-yl-furan-2-yl)-indan-1-one oxime;
5-(5-Piperidin-1-ylmethyl-2-pyrimidin-4-yl-furan-3-yl)-indan-1-one oxime;

5-[2-(2-Amino-pyrimidin-4-yl)-5-piperidin-1-ylmethyl-furan-3-yl]-indan-1-one oxime;
5-[5-(4-Hydroxy-piperidin-4-yl)-2-pyridin-4-yl-furan-3-yl]-indan-1-one oxime;
5-[2-Pyridin-4-yl-5-(1,2,3,6-tetrahydro-pyridin-4-yl)-furan-3-yl]-indan-1-one oxime;
5-(5-Piperidin-4-yl-2-pyridin-4-yl-furan-3-yl)-indan-1-one oxime;
5-{5-[1-(2-Methoxyethyl)-piperidin-4-yl]-2-pyridin-4-yl-furan-3-yl}-indan-1-one oxime;
5-(5-{1-[2-(4-Chloro-phenoxy)-ethyl]-piperidin-4-yl}-2-pyridin-4-yl-furan-3-yl)-indan-1-one oxime;
5-[5-(1-Cyclopentyl-piperidin-4-yl)-2-pyridin-4-yl-furan-3-yl]-indan-1-one oxime;
5-[5-(1-Cyclopropylmethyl-piperidin-4-yl)-2-pyridin-4-yl-furan-3-yl]-indan-1-one oxime;
5-{5-[1-(2-Morpholin-4-yl-ethyl)-piperidin-4-yl]-2-pyridin-4-yl-furan-3-yl}-indan-1-one oxime;
5-[5-(1-Methanesulfonyl-piperidin-4-yl)-2-pyridin-4-yl-furan-3-yl]-indan-1-one oxime;
5-{5-[1-(2-Dimethylamino-ethanoyl)-piperidin-4-yl]-2-pyridin-4-yl-furan-3-yl}-indan-1-one oxime;
5-{5-[1-(3-Piperidin-1-yl-propanoyl)-piperidin-4-yl]-2-pyridin-4-yl-furan-3-yl}-indan-1-one oxime;
5-(5-Piperidin-4-yl-3-pyridin-4-yl-furan-2-yl)-indan-1-one oxime;
5-{5-[1-(2-Methoxyethyl)piperidin-4-yl]-3-pyridin-4-yl-furan-2-yl}indan-1-one oxime;
5-[5-(1-Cyclopropylmethylpiperidin-4-yl)-3-pyridin-4-ylfuran-2-yl]indan-1-one oxime;
5-[5-(1-Cyclopentylpiperidin-4-yl)-3-pyridin-4-ylfuran-2-yl]indan-1-one oxime;
5-(5-{1-[2-(4-Chlorophenoxy)ethyl]-piperidin-4-yl}-3-pyridin-4-ylfuran-2-yl)indan-1-one oxime;
{4-[5-(1-Hydroxyiminoindan-5-yl)-4-pyridin-4-ylfuran-2-yl]piperidin-1-yl}acetonitrile;
5-{5-[1-(2-Hydroxyethyl)piperidin-4-yl]-3-pyridin-4-ylfuran-2-yl}indan-1-one oxime;
5-{5-[1-(2-Morpholin-4-ylethanoyl)piperidin-4-yl]-3-pyridin-4-ylfuran-2-yl}indan-1-one oxime;
5-{5-[1-(2-Piperidin-1-ylethanoyl)piperidin-4-yl]-3-pyridin-4-ylfuran-2-yl}indan-1-one oxime;
5-{5-[1-(2-Piperazin-1-ylethanoyl)piperidin-4-yl]-3-pyridin-4-ylfuran-2-yl}indan-1-one oxime;
5-(5-Piperidin-3-yl-2-pyridin-4-yl-furan-3-yl)-indan-1-one oxime;
5-[5-(1-Methyl-piperidin-3-yl)-2-pyridin-4-yl-furan-3-yl]-indan-1-one oxime;
N-Hydroxy-2-{3-[4-(1-hydroxyimino-indan-5-yl)-5-pyridin-4-yl-furan-2-yl]-piperidin-1-yl}-acetamidine;
5-{5-[1-(2-Methoxy-ethyl)-piperidin-3-yl]-2-pyridin-4-yl-furan-3-yl}-indan-1-one oxime;
5-[5-(1-Cyclopropylmethyl-piperidin-3-yl)-2-pyridin-4-yl-furan-3-yl]-indan-1-one oxime;
5-{5-[1-(2-Morpholin-4-yl-ethanoyl)-piperidin-3-yl]-2-pyridin-4-yl-furan-3-yl}-indan-1-one oxime;
5-{5-[1-(2-Piperidin-1-yl-ethanoyl)-piperidin-3-yl]-2-pyridin-4-yl-furan-3-yl}-indan-1-one oxime;
5-{2-Pyridin-4-yl-5-[1-(2-pyrrolidin-1-yl-ethanoyl)-piperidin-3-yl]-furan-3-yl}-indan-1-one oxime;
5-(5-{1-[2-(4-Methyl-piperazin-1-yl)-ethanoyl]-piperidin-3-yl}-2-pyridin-4-yl-furan-3-yl)-indan-1-one oxime;
5-[5-(1-{2-[4-(2-Methoxy-ethyl)-piperazin-1-yl]-ethanoyl}-piperidin-3-yl)-2-pyridin-4-yl-furan-3-yl]-indan-1-one oxime;
5-{5-[4-Hydroxy-1-(2-methoxyethyl)-piperidin-4-yl]-2-pyridin-4-yl-furan-3-yl}-indan-1-one oxime;
5-[5-(1-Cyclopropylmethyl-4-hydroxy-piperidin-4-yl)-2-pyridin-4-yl-furan-3-yl]-indan-1-one oxime; and
5-(5-Hydroxymethyl-2-pyridin-4-yl-furan-3-yl)indan-1-one oxime.

5. A pharmaceutical composition comprising an effective amount of a compound according to claim 1 or a pharmaceutically acceptable salt thereof and a pharmaceutically acceptable carrier.

6. A method for therapeutic treatment of cancer in a human, or other mammal, which comprises administering a therapeutically effective amount of a compound of formula (I) or a pharmaceutically acceptable salt thereof;
wherein the cancer selected from colorectal carcinoma or melanoma.

* * * * *